US 8,828,026 B2

(12) United States Patent
Ishioka et al.

(10) Patent No.: US 8,828,026 B2
(45) Date of Patent: Sep. 9, 2014

(54) TISSUE FASTENING APPARATUS

(75) Inventors: Ayano Ishioka, Tokyo (JP); Masatoshi Sato, Yokohama (JP); Shinji Takahashi, Tokyo (JP); Tatsutoshi Hashimoto, Tokyo (JP); Yusuke Nomura, Tokyo (JP); Kazushi Murakami, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 162 days.

(21) Appl. No.: 12/430,484

(22) Filed: Apr. 27, 2009

(65) Prior Publication Data

US 2010/0010509 A1     Jan. 14, 2010

Related U.S. Application Data

(63) Continuation-in-part of application No. 12/171,816, filed on Jul. 11, 2008, now abandoned, and a continuation-in-part of application No. 12/171,817, filed on Jul. 11, 2008, now Pat. No. 8,162,958.

(51) Int. Cl.
*A61B 17/10*     (2006.01)

(52) U.S. Cl.
USPC ......................................... 606/139; 606/142

(58) Field of Classification Search
USPC ........... 606/213, 215, 22, 223, 232, 198, 200, 606/151, 142, 139; 623/1.15, 1.22
See application file for complete search history.

(56) References Cited

U.S. PATENT DOCUMENTS 5,536,274 A    7/1996   Neuss
5,582,616 A * 12/1996   Bolduc et al. ................. 606/143
5,830,221 A * 11/1998   Stein et al. .................... 606/157
6,113,611 A *   9/2000   Allen et al. .................... 606/151
6,117,157 A     9/2000   Tekulve (Continued)

FOREIGN PATENT DOCUMENTS

JP    UM-A-05-070549     9/1993
JP    A-07-308331          11/1995

(Continued)

OTHER PUBLICATIONS

Partial European Search Report dated May 3, 2010.

(Continued)

*Primary Examiner* — Dianne Dornbusch
(74) *Attorney, Agent, or Firm* — Scully, Scott, Murphy & Presser, P.C.

(57) ABSTRACT

A tissue fastening apparatus includes a tissue fastening tool, with fastens a first biological tissue and a second biological tissue so as to bring the tissues into close contact and an applicator for indwelling the tissue fastening tool. The tissue fastening tool is made of an elastic wire rod and is wound in a coil shape. The applicator includes a needle tube accommodated in an inner cavity with the tissue fastening tool stretched, a stylet inserted into the inner cavity of the needle tube nearer to the proximal side than the tissue fastening tool, and a rotating mechanism that rotates the stylet around an axis when the stylet is moved toward a distal end of the needle tube. The tissue fastening tool and the stylet are disengageably engaged with each other and integrally and rotatably connected with each other. The rotating mechanism rotates the stylet in a direction opposite to the winding direction of the tissue fastening tool as seen from the proximal side.

14 Claims, 23 Drawing Sheets

(56) References Cited

U.S. PATENT DOCUMENTS

| | | | |
|---|---|---|---|
| 6,551,340 B1 * | 4/2003 | Konya et al. | 606/191 |
| 6,635,066 B2 | 10/2003 | Tanner et al. | |
| 6,663,633 B1 * | 12/2003 | Pierson, III | 606/148 |
| 6,790,218 B2 | 9/2004 | Jayaraman | |
| 6,837,893 B2 | 1/2005 | Miller | |
| 6,986,784 B1 * | 1/2006 | Weiser et al. | 623/1.1 |
| 7,131,979 B2 * | 11/2006 | DiCarlo et al. | 606/144 |
| 7,637,946 B2 | 12/2009 | Solem et al. | |
| 7,722,636 B2 * | 5/2010 | Farnan | 606/200 |
| 2002/0013605 A1 | 1/2002 | Bolduc et al. | |
| 2003/0014127 A1 | 1/2003 | Talja et al. | |
| 2003/0225420 A1 | 12/2003 | Wardle | |
| 2004/0073237 A1 | 4/2004 | Leinsing | |
| 2005/0143763 A1 * | 6/2005 | Ortiz et al. | 606/153 |
| 2005/0267495 A1 * | 12/2005 | Ginn et al. | 606/151 |
| 2006/0212047 A1 | 9/2006 | Abbott et al. | |
| 2007/0123928 A1 * | 5/2007 | Farnan | 606/200 |
| 2007/0225737 A1 * | 9/2007 | Messerly et al. | 606/151 |
| 2008/0004640 A1 * | 1/2008 | Ellingwood | 606/151 |
| 2008/0015633 A1 * | 1/2008 | Abbott et al. | 606/207 |
| 2008/0208214 A1 * | 8/2008 | Sato et al. | 606/139 |
| 2009/0069822 A1 * | 3/2009 | Takahashi et al. | 606/139 |
| 2010/0010508 A1 | 1/2010 | Takahashi et al. | |
| 2010/0010520 A1 | 1/2010 | Takahashi et al. | |

FOREIGN PATENT DOCUMENTS

| | | |
|---|---|---|
| JP | T-2000-514336 A | 10/2000 |
| JP | T-2003-517869 A | 6/2003 |
| JP | 2005-193044 | 7/2005 |
| JP | T-2009-508536 A | 3/2009 |
| WO | WO 97/27898 A1 | 8/1997 |
| WO | WO 97/32527 | 9/1997 |
| WO | WO 98/02100 A1 | 1/1998 |
| WO | WO 01/45571 A1 | 6/2001 |
| WO | WO 02/19923 A1 | 3/2002 |
| WO | WO 03/105703 A2 | 12/2003 |
| WO | WO 2004/026113 A2 | 4/2004 |
| WO | WO 2007/005996 A2 | 1/2007 |

OTHER PUBLICATIONS

Partial European Search Report dated May 31, 2010.
Partial European Search Report dated Oct. 25, 2011 received in related EP 11003621.7-2310.
U.S. Official Action mailed Dec. 15, 2011 in related U.S. Appl. No. 12/430,442.
U.S. Office Action dated Jun. 16, 2011, received in related U.S. Appl. No. 12/171,816.
U.S. Office Action dated Jul. 27, 2011, received in related U.S. Appl. No. 12/430,442.
U.S. Office Action dated Jul. 12, 2011, received in related U.S. Appl. No. 12/171,817.
Japanese Official Action mailed May 8, 2012 in corresponding Japanese Patent Application No. 2009-146917, together with English language translation.
Chinese Office Action dated Feb. 11, 2014 in corresponding Chinese Patent Application No. 201210193072.3.
Japanese Office Action dated Jan. 28, 2014 in corresponding Japanese Patent Application No. 2012-113240.

* cited by examiner

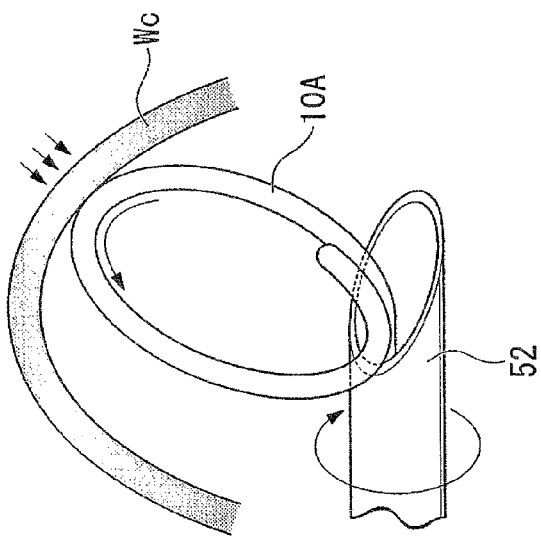
FIG. 13A  FIG. 13B  FIG. 13C
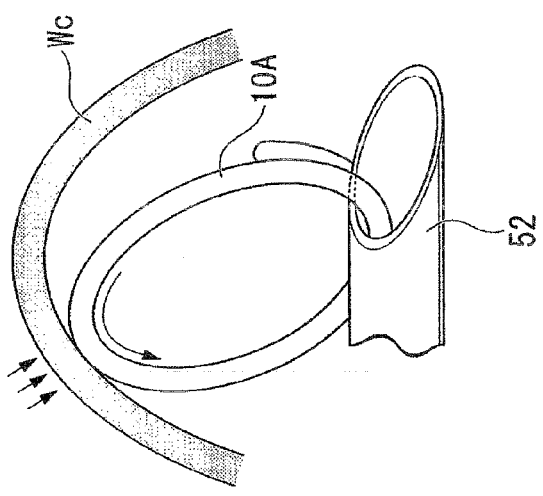
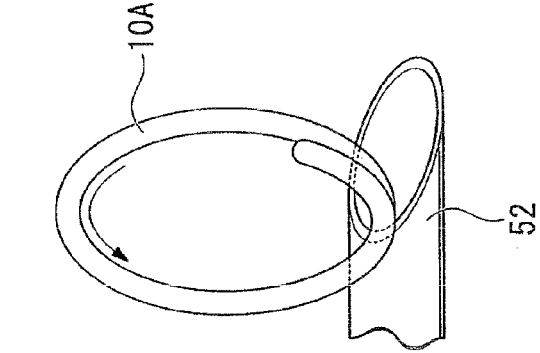
FIG. 13D
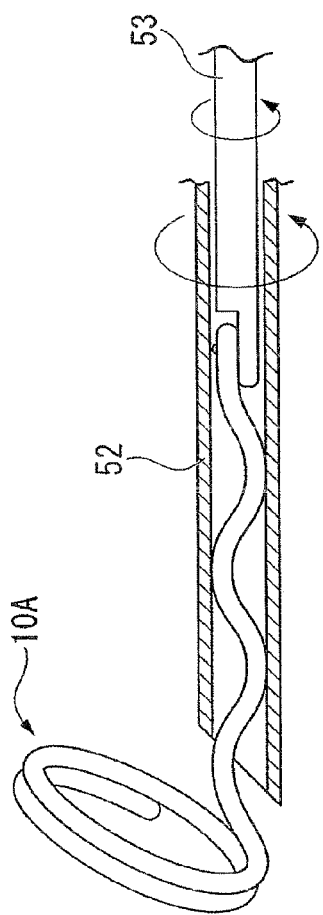

TISSUE FASTENING APPARATUS

REFERENCE OF RELATED APPLICATION

The present application is a continuation-in-part application of "Tissue fastening tool" of U.S. application Ser. No. 12/171,816 filed on Jul. 11, 2008 now abandoned, "Tissue fastening tool, applicator for indwelling the same within a body, and tissue fastening method through natural orifice" of U.S. application Ser. No. 12/171,817, now U.S. Pat. No. 8,162,958, filed on Jul. 11, 2008, and claims priority on the two applications, the content of which is incorporated herein by reference.

BACKGROUND OF THE INVENTION

1. Field of the Invention

The present invention relates to a tissue fastening tool that fixes a tissue through a natural orifice, and an applicator to be used when the tissue fastening tool is indwelled within a body.

2. Description of the Related Art

Laparoscopic surgery which utilizes transcutaneous insertion of treatment tools is well known as a procedure of treating body organs. This method is less invasive compared to incising the abdomen, and quick recovery is common.

The treatment tool used for laparoscopic surgery involves a hard shaft being inserted into a body transcutaneously and has forceps or the like provided at the distal end of the shaft. For example, a treatment tool used in applications such as connecting hollow organs is disclosed in Japanese Unexamined Patent Application, First Publication No. 2005-193044. This intraluminal anastomosis device has a grasper that is openably and closably attached to the distal end of the shaft, and a fastening tool inserted into the shaft. The fastening tool can be pushed out of the distal end of the shaft by a projection mechanism device located proximally with respect to the operator. The fastening tool is manufactured by heat-treating a shape memory alloy into a flat coil shape and it is inserted into the shaft in an extended condition. When the fastening tool is used, the fastening tool is pushed out by the projection mechanism and is pierced into the body. The fastening tool is heated by the body temperature and is returned to its coil shape. The hollow organs are joined by the returned fastening tool.

Another example of dispensing the fastening tool is disclosed in International Publication Number WO2002/019923. Here, the fastening tool is pushed out from the needle and dispensed to the tissue. For this reason, a stopper is provided to control the depth when a needle pierces a tissue and the amount of the fastening tool to be dispensed to the tissue. When performing this treatment, the instrument containing the fastening tool and the needle butts against the tissue. If the needle advances to pierce the tissue, the position of the fastening tool is fixed by the stopper Thereafter, the needle is pulled out of the tissue. The fastening tool does not move because of the stopper; therefore, its distal end portion remains inside the tissue. When the instrument is removed from the tissue, the rest of the fastening tool remains outside the tissue. When the fastening tool is returned to its coil shape, the tissue is fastened.

SUMMARY OF THE INVENTION

The present invention provides a tissue fastening apparatus including a tissue fastening tool which fastens a first biological tissue and a second biological tissue so as to bring the tissues into close contact with each other, and an applicator for indwelling the tissue fastening tool. The tissue fastening tool is made of an elastic wire rod and is wound in a coil shape. The applicator includes a needle tube accommodated in an inner cavity with the tissue fastening tool stretched, a stylet inserted into the inner cavity of the needle tube nearer to the proximal side than the tissue fastening tool, and a rotating mechanism that rotates the stylet around an axis when the stylet is moved toward a distal end of the needle tube. The tissue fastening tool and the stylet are disengageably engaged and integrally and rotatably connected with each other. The rotating mechanism rotates the stylet in a direction opposite to the winding direction of the tissue fastening tool as seen from the proximal side.

BRIEF DESCRIPTION OF THE DRAWINGS

FIGS. 13A to 13D are views showing the operation of the tissue fastening tool and the needle tube.

DETAILED DESCRIPTION OF THE INVENTION

Figure 1:
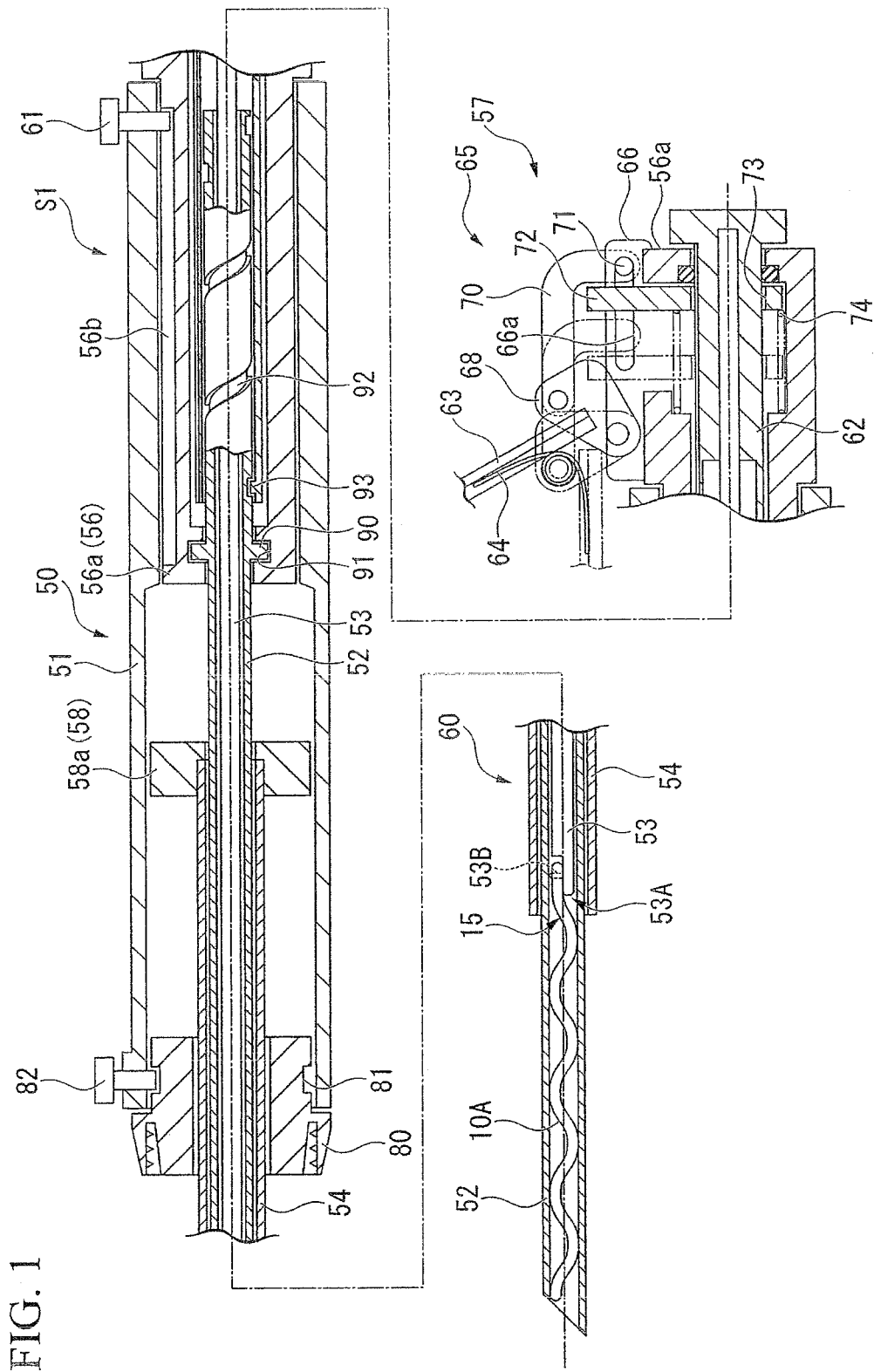
FIG. 1 is a sectional view showing a tissue fastening tool and applicator of according to the one embodiment of the present invention.

Hereinafter, one embodiment of the invention will be described. A tissue fastening apparatus S1 in the present embodiment is an apparatus which integrally fixes a second biological tissue to a first biological tissue and causes the tissues to communicate with each other. As shown in FIG. 1, the apparatus includes a tissue fastening tool 10A, and an applicator 50.

Note that the first and second biological tissues are not limited to different organs. For example, a region of an organ may be referred to as the first biological tissue and a different region of the same organ may be referred to as the second biological tissue, so as to include fixing these two regions within the same organ. In the present embodiment, a treatment to fix a common biliary duct as the second biological tissue to a duodenum as the first biological tissue and causes both the organs to communicate with each other will be described as an example.

Figure 2:
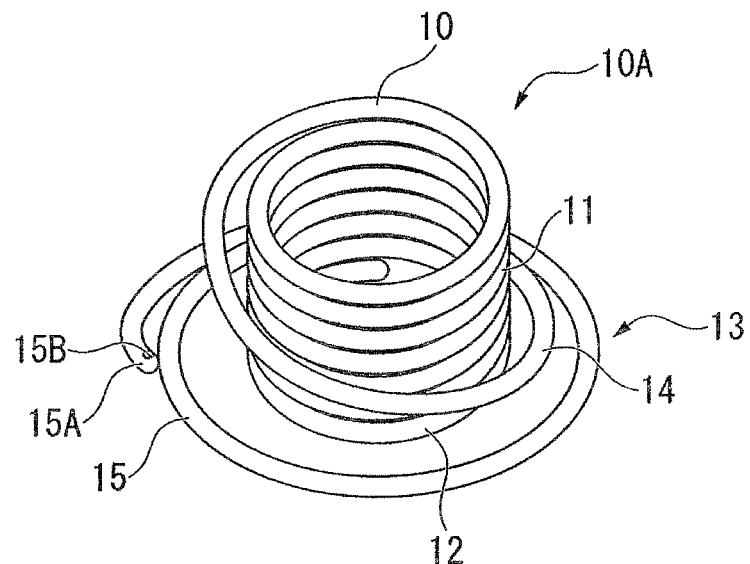
FIG. 2 is a perspective view of the tissue fastening tool.
Figure 3:
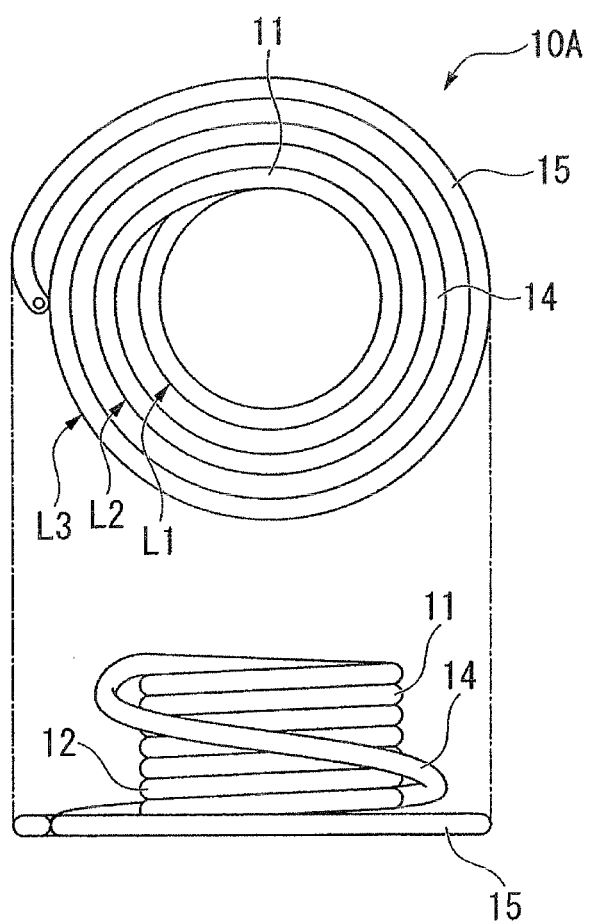
FIG. 3 is a front view and plan view of the tissue fastening tool.

FIGS. 2 and 3 are views showing the tissue fastening tool 10A of the present embodiment. As shown in FIG. 2, the tissue fastening tool 10A is provided with a first tissue fixing section 11 which is hooked onto the duodenum, a second tissue fixing section 12 which is hooked onto the common biliary duct adjacent to the duodenum, and an outer peripheral spring portion 13 which is connected to the first tissue fixing section 11.

The tissue fastening tool 10A is formed of a high elastic metal wire rod 10 (hereinafter referred to as "metal wire rod") in which all portions, i.e., the first tissue fixing section 11, the second tissue fixing section 12, and the outer peripheral spring portion 13 are wound into a coil shape. The first tissue fixing section 11 and the second tissue fixing section 12 have the same loop diameter, and are formed so that their mutual loops are coaxial with each other.

The outer peripheral spring portion 13 is provided with a spring portion 14 that extends from an end of the first tissue fixing section 11, and an end coil portion 15 that extends from an end of the spring portion 14.

The spring portion 14 extends toward the second tissue fixing section 12 from the end of the first tissue fixing section 11 while forming a larger loop than the first tissue fixing section 11 and the second tissue fixing section 12. The loop that the spring portion 14 forms gradually becomes larger as it goes towards the second tissue fixing section 12. It is noted that this shape is not indispensable to the present invention, for example, the spring portion 14 may extend toward the second tissue fixing section 12, while forming a loop of the same diameter.

Since the spring portion 14 extends towards the second tissue fixing section 12, as shown in FIG. 3, the metal wire rod 10 that forms the spring portion 14 has an angle so as to incline with respect to the axis of a loop (hereinafter referred to as a "basic loop") of the first tissue fixing section 11 and the second tissue fixing section 12.

It is preferable that the spring portion 14 be formed so as to have one or more integer turns.

Figure 4A:
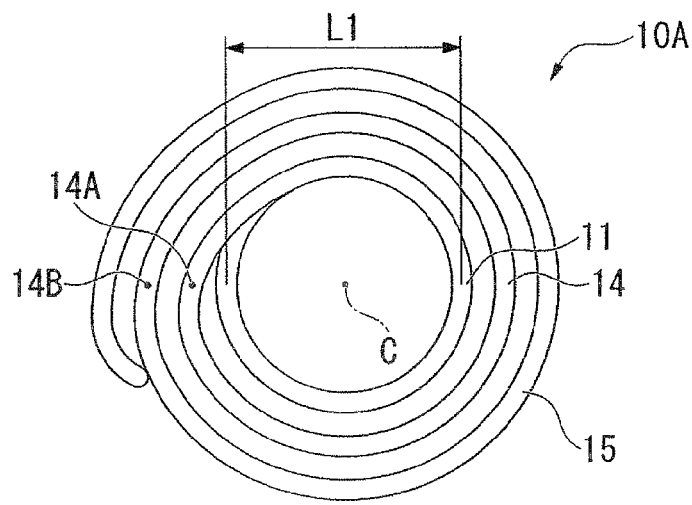
FIGS. 4A and 4B are views showing the relationship between the outer peripheral spring of the tissue fastening tool, and an acting force.

The "one or more integer turns" means that an end 14A of the spring portion 14 on the side of the first tissue fixing section 11 and an end 14B of the spring portion 14 on the side of the end coil portion 15 are aligned on the same straight line as the center C without pinching the center C of a basic loop L1 therebetween in plan view of the tissue fastening tool 10A as shown in FIG. 4A.

Figure 4B:
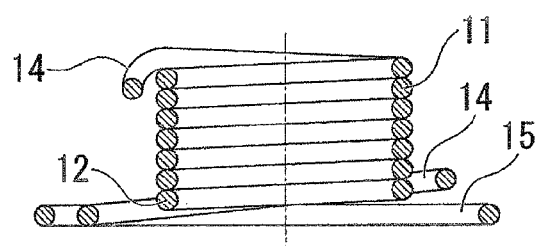
Figure 4C:
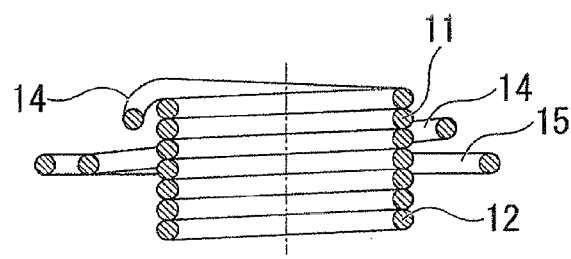
FIGS. 4C and 4D are views showing a state where the tissue fastening tool shown in FIG. 4A is indwelled in a tissue.
Figure 4D:
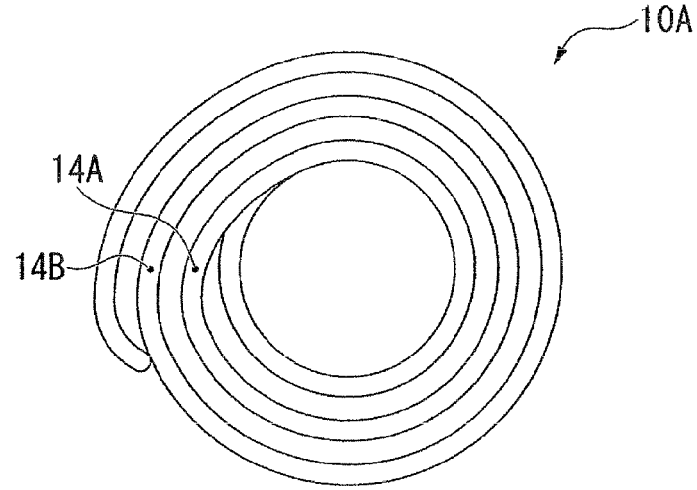

If the spring portion 14 has one or more integer turns, the spring portion 14 is uniformly distributed radially outside the basic loop L1 like FIG. 4B in any kind of cross-section when the tissue fastening tool 10A is seen in the axial cross-section that passes through the center C. Although the state where the spring portion 14 is set to have one turn is shown as an example in FIG. 4B, the spring portion will be put in the same state even at two or more turns so long as the number of turns is an integer. Accordingly, the forces that the spring portion 14 act on the first tissue fixing section 11 and the second tissue fixing section 12 in the orthogonal direction (in a cross-sectional direction) to the axis of the basic loop L1 becomes equal to each other. As a result, as shown in FIGS. 4C and 4D, even when the tissue fastening tool is indwelled in the tissue, the basic loop of the first tissue fixing section 11 and the second tissue fixing section 12 does not cause axial deviation, and the shape thereof is stable.

An example in which the spring portion 14 is set to have a ½ turn as an example that is not an integer turn is shown in FIGS. 5A to 5D. In the tissue fastening tool 110A, ends 114A and 114B of the outer peripheral spring 114 are located on the same straight line as the center C, pinching the centre C of the basic loop L1 therebetween.

Figure 5A:
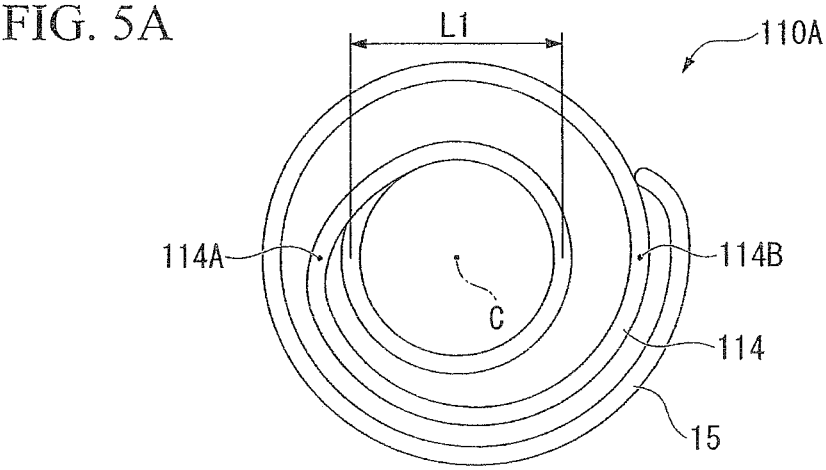
FIGS. 5A and 5B are views showing the relationship between the outer peripheral spring of the tissue fastening tool, and an acting force.
Figure 5B:
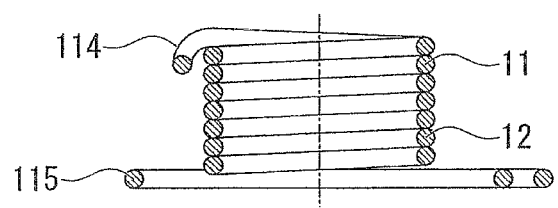
Figure 5C:
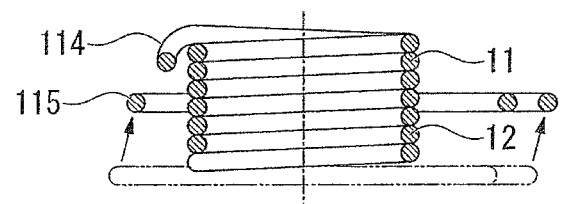
FIGS. 5C and 5D are views showing a state where the tissue fastening tool shown in FIG. 5A is indwelled in a tissue.
Figure 5D:
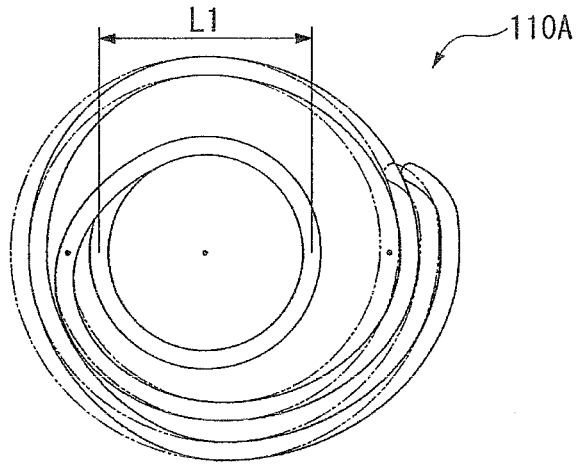

In this case, as shown in FIG. 5B, depending on how to take an axial cross-section through the center C, the balance of the amounts of the spring portion 14 that exist on both sides of the first tissue fixing section 11 and the second tissue fixing section 12 is lost. If the tissue fastening tool 110A with such a spring portion 114 is indwelled in the tissue, as shown in FIGS. 5C and 5D, axial deviation occurs between the basic loop L1, and the loop L3 formed by the end coil portion 15. As a result, since an unbalanced force acts in the cross-sectional direction and the first tissue fixing section 11 and the second tissue fixing section 12 becomes a hindrance to sufficiently exhibit a tissue fastening force as will be described later, the tissue fastening tool is not preferable.

The angle at which the metal wire rod 10 extends changes at the end 14B at a connecting portion between the spring portion 14 and the end coil portion 15, and the end coil portion 15 forms a loop vertical to the axis of the basic loop L1. Accordingly, the loop of the end coil portion 15 is parallel to the basic loop L1. As shown in FIG. 2, the end 15A of the end coil portion 15 is provided with a through hole 15B, and the degree of bending is adjusted in a place where the end coil portion 15 which has formed one or more turns of loop so that the end 15A comes in contact with other parts of the end coil portion 15.

The loop that the end coil portion 15 forms has a larger diameter than the loop that the spring portion 14 forms. Accordingly, as shown in the plan view of FIG. 3, if the tissue fastening tool 10A is seen from the direction of the basic loop axis L1, the basic loop L1 exists on the innermost side, the second loop L2 that the spring portion 14 forms, exists outside the basic loop and the third loop L3 that the end coil portion 15 forms is located outside the second loop. The basic loop L1, the second loop L2, and the third loop L3 do not overlap each other in the radial direction of the basic loop L1.

The tissue fastening tool 10A is stretched, and one end thereof pierces the biological tissue, and one tissue fixing section, for example, the second tissue fixing section 12, is made to sequentially pass through the wall of the duodenum and the wall of the common biliary duct. The second tissue fixing section 12 which has penetrated the wall of the duodenum and the wall of the common biliary duct is released from its constraint inside the common biliary duct, is returned to its original coil shape, and is hooked onto the common biliary duct. On the other hand, the first tissue fixing section 11 is released from its constraint inside the duodenum, is restored to its original coil shape, and is hooked onto the duodenum. As the first tissue fixing section 11 is hooked onto the duodenum and the second tissue fixing section 12 is hooked onto the common biliary duct, the wall of the duodenum and the wall of the common biliary duct are fastened and integrally fixed such that both the walls are pushed against each other. At this time, the end coil portion 15 of the outer peripheral spring portion 13 abuts on the wall of the duodenum around the first tissue fixing section 11, and the spring portion 14 biases the end coil portion 15 so as to push the wall against the common biliary duct. These points will be described in detail in the description of the operation when the tissue fastening apparatus S1 is used.

The applicator 50 is a tool to indwell the tissue fastening tool 10A within the body, and as shown in FIG. 1, the applicator is provided with a main body 51, a needle tube 52, a stylet (fastening tool pusher) 53, and a sheath 54.

The main body 51 is formed in a tubular shape, and has a needle tube operating section 56, a stylet operating section 57, and a ring member (sheath operating section) 58a for advancing and retreating the sheath 54 with respect to the main body 51. All of the needle tube 52, the stylet 53 and the sheath 54 are flexible, and are disposed coaxially with each other. These constitute an insertion section 60 that is inserted into an operating channel of an insertion section of an endoscope, and thus, the insertion section 60 is longer than the operating channel of the endoscope.

The needle tube 52 is used in a state which accommodates the tissue fastening tool 10A has been extended. The distal end face of the needle tube 52 is formed with respect to the longitudinal direction of the needle tube 52. Thereby, the distal end of the needle tube 52 is sharply finished. A proximal end of the needle tube 52 is connected to the needle tube operating section 56 provided at a rear portion of the main body 51.

In addition, an electrode may be provided at a distal end of the needle tube 52, and the needle tube 52 may pierce the wall of the duodenum and the wall of the common biliary duct while cauterizing the biological tissue. In this case, the distal end of the needle tube tool 52 may not be sharply formed.

The stylet 53 is shaft-shaped, is inserted into the needle tube 52 so as to be movable within the needle tube, and pushes the tissue fastening tool 10A inserted into the needle tube 52 out of the distal end of the needle tube 52. A distal end 53A of the stylet 53 is formed with a projection 53B, and as shown in FIG. 1, the tissue fastening tool 10A is accommodated within the needle tube 52 in a state where the through hole 15B of the end coil portion 15 and the projection 53B are engaged with each other.

For this reason, the tissue fastening tool 10A integrated with the stylet 53, is able to advance and retreat with the stylet 53, and rotates inside the needle tube 52 if the stylet 53 rotates about its axis. The gap between the inner cavity of the needle tube 52 and the stylet 53 is set to be smaller than the diameter of the metal wire rod 10 that constitutes the tissue fastening tool 10A. Therefore, the engagement between the through hole 15B and the projection 53B are not released within the needle tube 52. In addition, in making the gap between the inner cavity of the needle tube 52 and the stylet 53 small, the diameter of the stylet 53 may be increased other than increasing the protruding length of the projection 53B. Moreover, the release of the above engagement may be suppressed by increasing the maximum diameter of the metal wire rod 10 to limit the movable range within the needle tube 52 of the metal wire rod 10 instead of making the gap between the inner cavity of the needle tube 52 and the stylet 53 small.

The proximal end of the stylet 53 is connected to the stylet operating section 57 provided inside the needle tube operating section 56 as will be described later.

The sheath 54 is a flexible tubular member, and the needle tube 52 is inserted through the inner cavity. A distal end face of the sheath 54 is flatly formed in a perpendicular direction to the longitudinal direction of the sheath 54.

The needle tube operating section 56 includes a first cylindrical shaft 56a inserted from the rear end of the main body 51 thereinto. The outer diameter of the first shaft 56a is slightly smaller than the inner diameter of a rear portion of the main body 51. Therefore, the first shaft 56a is able to slide with respect to the inner surface of the rear portion of the main body 51. The proximal end of the needle tube 52 is anchored to the distal end face of the first shaft 56a inserted into the main body 51 so that the longitudinal direction of the needle tube 52 coincides with the longitudinal direction of the first shaft 56a. The needle tube 52 can change its position relative to the main body 51 by making the first shaft 56a slide with respect to the main body 51.

An internal thread hole is formed in a radial direction of the main body 51 at the rear portion of the main body 51, and an external thread 61 is screwed into the internal thread hole. The distal end of the external thread 61 projects into the inner cavity of the main body 51. On the other hand, a groove 56b is formed along the longitudinal direction of the first shaft 56a on the outer surface of the first shaft 56a. The distal end of the external thread 61 is loosely fitted into the groove 56b. Thereby, the groove 56b controls the movable range of the first shaft 56a with respect to the main body 51. If the external thread 61 is further screwed into the internal thread hole and its distal end is pressed against the bottom surface of the groove 56b, it is possible to hold the first shaft 56a at an arbitrary position with respect to the main body 51.

The stylet operating section 57 includes a second cylindrical shaft 62 inserted from the rear end of the first shaft 56a thereinto, a lever 63 rockably supported by the first shaft 56a which supports the needle tube 52, a torsion coil spring 64 which biases the lever 63 in a direction away from the main body 51, and a link mechanism 65 which converts the rocking of the lever 63 into a liner motion along the needle tube 52 of the stylet 53.

A proximal end of the stylet 53 is inserted from the distal end of the second shaft 62 thereinto, and is anchored to the second shaft 62 so that the longitudinal direction of the stylet 53 coincides with the longitudinal direction of the second shaft 62. The stylet 53 can change its position relative to the needle tube 52 by making the second shaft 62 slide with respect to the first shaft 56a.

The outer periphery of the needle tube 52 is provided with a projection 90, and the projection 90 fits into a ring groove 91 formed at an inner periphery of a distal end of the needle tube operating section 56. Thereby, the needle tube 52 is rotatable relative to the needle tube operating section 56, and is not relatively movable in the axial direction. A spiral groove 92 is formed on the outer peripheral surface nearer to the proximal side than the projection 90 of the needle tube 52.

A pin-shaped projection 93 is provided on an inner peripheral surface of the second shaft 62 that faces the outer peripheral surface of the needle tube 52, and the projection 93 is engaged with a spiral groove 92 (hereinafter referred to as the "spiral groove 92"). Additionally, the outer periphery of the second shaft 62 is formed of a longitudinal groove 94, and a plate member 72 is attached to the outside of the second shaft 62 (refer to FIG. 8B). The projection 95 is provided an inner peripheral portion of the plate member 72, and the projection 95 is fitted to the longitudinal groove 94. Thereby, the second shaft 62 is relatively movable in the axial direction while its rotation relative to the plate member 72 is stopped. The ring groove 91 and the projection 90, and the spiral groove 92 and the projection 93 which correspond to each other constitutes a rotating mechanism 96 that rotates the needle tube 52 when the second shaft 62 whose rotation is stopped advances or retracts along the axial direction.

When the needle tube 52 rotates in conjunction with the axial movement of the second shaft 62, the shape of the spiral groove 92 is set so that the rotational direction of the needle tube 52 and the coil winding direction of the tissue fastening tool 10A are opposite to each other. Furthermore, although the stylet 53 pushes the tissue fastening tool 10A out of the distal end of the needle tube 52, the spiral shape of the spiral groove 92 is set so that the needle tube 52 makes one rotation whenever the tissue fastening tool 10A is pushed out by a length equivalent to one coil winding by the axial movement of the second shaft 62. Accordingly, the length of the spiral groove per one rotation of the needle tube is different in the region of the spiral groove 92 that is engaged with the projection 93 when the first tissue fixing section 11 and the second tissue fixing section 12 are pushed out, and the region of the spiral groove 92 that is engaged with the projection 93 when the outer peripheral spring portion 13 is pushed out.

In addition, in this embodiment, the spiral groove 92 and the projection 93 are disposed at the outer periphery of the needle tube 52 and the inner periphery of the second shaft 62, respectively. However, the present invention is not limited thereto; in reverse, the projection and the spiral groove may be disposed at the outer periphery of the needle tube 52 and the inner periphery of the second shaft 62, respectively, or the spiral shape may be constituted from a convex instead of the groove, and a rotating mechanism may be constituted using a projection or the like which is engageable with this convex.

The link mechanism 65 includes a base member 66, a bracket 68, a bar 70, a plate member 72 and a compression coil spring 74. The base member 66 is fixed to an outer surface of the first shaft 56a. The bracket 68 is journalled to the base member 66. The lever 63 has a lower end fixed to the bracket 68. The bar 70 has one end journalled to the bracket 68 and the other end journalled to the base 66. A pin 71 that is provided at the other end of the bar 70 is loosely fitted into a long hole 66a formed in the base member 66 along the sliding direction of the second shaft 62.

The plate member 72 is formed with a hole 73 with a diameter that is larger than the outer diameter of the second shaft 62, and the second shaft 62 inserted into the first shaft 56a passes through the hole 73. The difference between the outer diameter of the second shaft 62 and the inner diameter of the hole 73 is extremely small. And if the plate member 72 is tilted and moved in the longitudinal direction of the second shaft 62, i.e., in the direction of insertion of the second shaft 62 into the first shaft 56a, the inner face of the hole 73 interferes with the outer surface of the second shaft 62. Thus, friction is created, and the force that is applied to the plate member 72 acts on the second shaft 62.

The compression coil spring 74 is disposed inside the first shaft 56a, and biases the plate 72 in a direction opposite to the direction of insertion of the second shaft 62 into the first shaft 56a.

If the lever 63 is moved closer to the main body 51, the bar 70 is pulled toward the front of the main body 51 via the bracket 68 and the other end of the bar 70 is moved along the long hole 66a. The plate member 72 is pushed by the other end of the bar 70, and is moved in the direction of insertion of the second shaft 62 into the first shaft 56a against the compression coil spring 74. At this time, since the plate member 72 is slightly tilted and friction is caused between the plate member and the second shaft 62, a force that is applied to the plate 72 acts on the second shaft 62, and the second shaft 62 is press-fitted into the first shaft 56a.

If the lever 63 is released, the torsion coil spring 64 separates the lever 63 from the main body 51 and the compression coil spring 74 pushes only the plate member 72 back to its initial position without creating any friction between the second shaft 62 and the plate member 72.

Since the travel distance of the other end of the bar 70 per operation of the lever 63 is always constant, the length of insertion of the second shaft 62 into the first shaft 56a per operation of the lever 63 is also always constant. Accordingly, it is possible to control the length of insertion of the second shaft 62 into the first shaft 56a, i.e., the distance of insertion of the stylet 53 into the needle tube 52 according to the number of operations of the lever 63. This denotes that it is also possible to control the length of the tissue fastening tool 10A pushed out of the distal end of the needle tube 52 according to the number of operations of the lever 63.

When the tissue fastening tool 10A is formed into a coil shape with the loop outside the needle tube 52 like the present embodiment, it is preferable that the insertion length of the stylet 53 per operation of the lever 63 be about n or about 1/n times (n is a natural number) the loop of the tissue fastening tool 10A.

For example, if the insertion length of the stylet 53 per operation of the lever 63 is substantially equal to the circumference of the tissue fastening tool 10A, the tissue fastening tool 10A is pushed out of the distal end of the needle tube 52 by one turn whenever the lever 63 is operated once. Furthermore, when the second tissue fixing section 12 consists of two turns of the tissue fastening tool 10A, only the second tissue fixing section 12 can be pushed out of the distal end of the needle tube 52 if the lever 63 is operated twice.

Additionally, if the insertion length of the stylet 53 per operation of the lever 63 is substantially equal to the half of the circumference of the tissue fastening tool 10A, the tissue fastening tool 10A is pushed out of the distal end of the needle tube 52 by a half turn whenever the lever 63 is operated once. Furthermore, when the second tissue fixing section 12 consists of two turns of the tissue fastening tool 10A, only the second tissue fixing section 12 can be pushed out of the distal end of the needle tube 52 if the lever 63 is operated four times.

Moreover, it is also possible to set the lengths of the spring portion 14 of the outer peripheral spring portion 13, and the end coil portion 15 to the integral multiple of the insertion length of the stylet 53 per operation of the lever 63, thereby exactly pushing only the spring portion 14 or the end coil portion 15 out of the needle tube 52.

A mouthpiece 80 is inserted into the distal end of the main body 51. Since the mouthpiece 80 is formed with an inside screw 80A, the applicator 50 can be fixed to the endoscope by screwing the inside screw 80A into the mouthpiece of the endoscope. A groove 81 is formed along a peripheral direction on the outer surface of the mouth piece 80. On the other hand, the main body 51 is formed with an internal thread hole that extends in the radial direction, and the external thread 82 is screwed into the internal thread hole. The distal end of the external thread 82 projects into the inside of the main body 51. The distal end of the external thread 82 is loosely fitted into the groove 81 of the mouthpiece 80. This can freely rotate the whole applicator 50 with respect to the mouthpiece 80 fixed to the endoscope. If the external thread 82 is further screwed into the internal thread hole and the distal end thereof is pushed against a bottom surface of the groove 81, the main body 51 can be positioned and held in an arbitrary peripheral position with respect to the mouthpiece 80.

Figure 6:
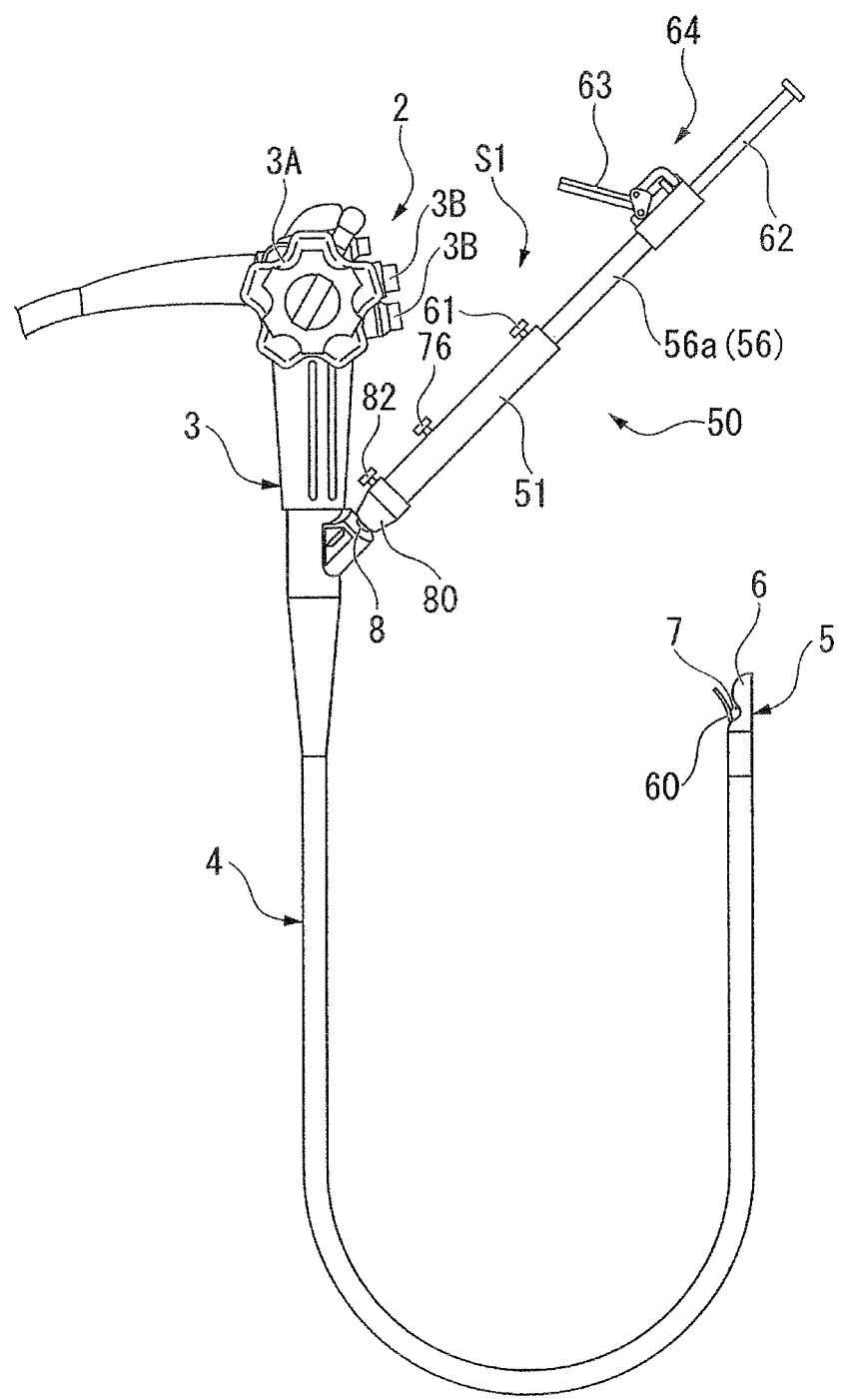
FIG. 6 is a view showing a state where the applicator has been inserted into an endoscope.

FIG. 6 shows a linear scanning type ultrasonic endoscope 2 (hereinafter simply referred to as an "endoscope") as an example of an endoscope to be used together with the tissue fasting apparatus S1. The endoscope 2 is provided with a flexible insertion portion 4 that extends from the operation portion 3 to be used outside a body.

A knob 3A for curving the distal end portion of the insertion portion 4 and various buttons 3B are disposed in the operation portion 3. A cover 5 is attached to the distal end of the insertion portion 4. An ultrasonic device 6 is attached to the cover 5.

The ultrasonic device 6 is bulged on a plane including the axis of the insertion portion 4. A plurality of ultrasonic vibrators is disposed along a circular-arc outer periphery of the device. Furthermore, the endoscope 2 is provided with a standing base 7 for delivery of the distal end portion of the applicator 50 in a lateral direction. The direction of the insertion portion 60 of the applicator 50 delivered from the distal end of the insertion portion 4 can be adjusted by operating the standing base 7 proximally with respect to an operator. The endoscope 2 may be provided with other probe-types of ultrasonic devices. Additionally, an endoscope that is not provided with the ultrasonic device 6 can also be used. In this case, any ultrasonic device used outside the body, such as an X-ray device, a magnetic resonance imaging (MRI) device, or a computerized tomography (CT) device may be used jointly.

Figure 7:
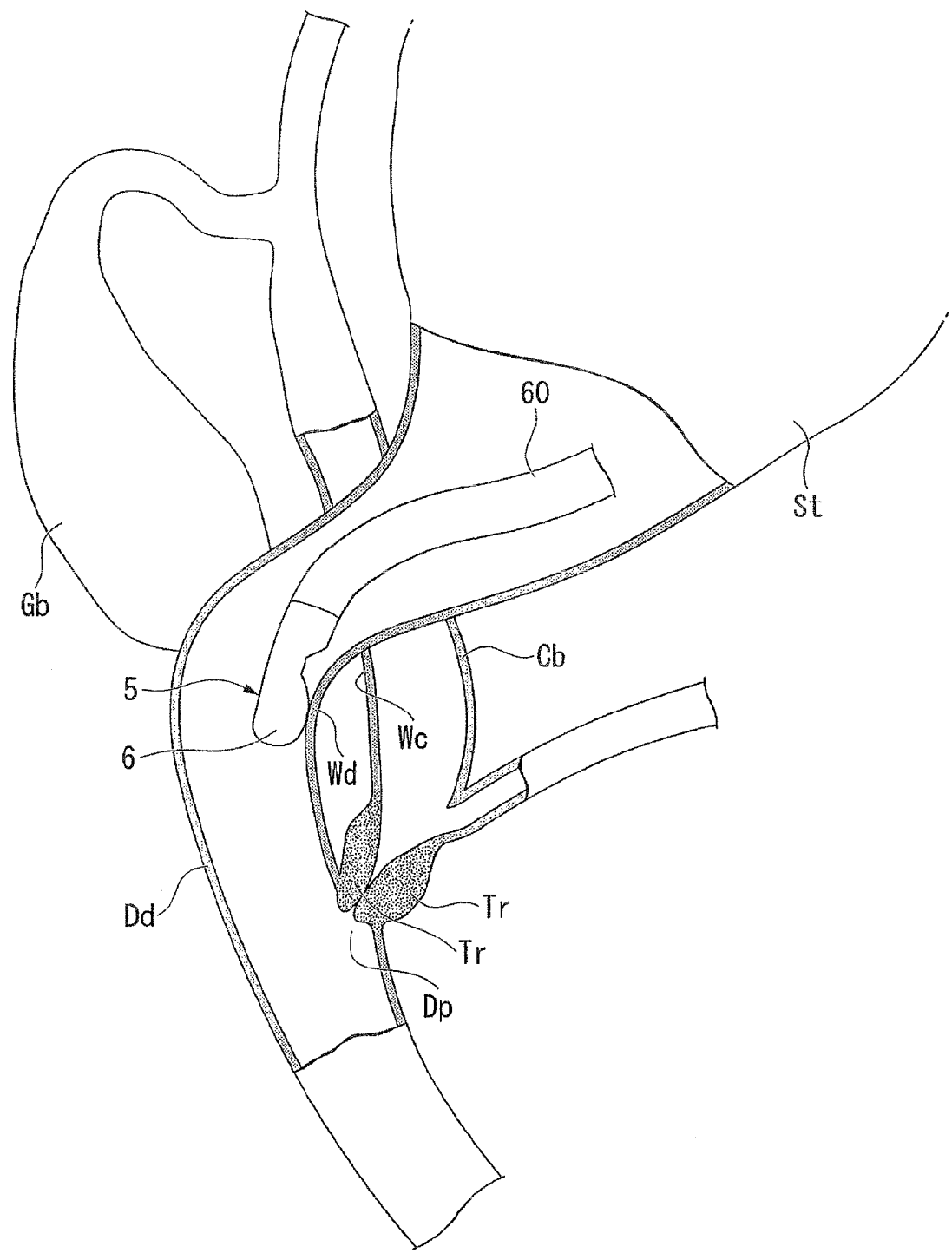
FIG. 7 is a view showing the operation of the endoscope when the applicator is used.

Next, the procedure of indwelling the tissue fastening tool 10A within the body cavity using the tissue fastening apparatus S1 configured as described above, and integrally fixing a duodenum and a common biliary duct to make both to communicate with each other will be described. For example, as shown in FIG. 7, this kind of procedure is performed when a duodenal papilla Dp is obstructed by a tumor Tr preventing bile drainage, and consequently the bile assimilates in the blood causing jaundice. This procedure enables the direct drainage of bile from the common biliary duct Cb to the duodenum Dd.

First, the insertion portion 4 of the endoscope 2 is inserted from the patient's mouth. The endoscope 2 is inserted into the duodenum Dd that is an upper alimentary canal. The condition outside the duodenum Dd is investigated by the ultrasonic device 6, and an appropriate location for the procedure close to the common biliary duct Cb is searched on the side of the stomach St rather than the duodenal papilla Dp.

Figure 8:
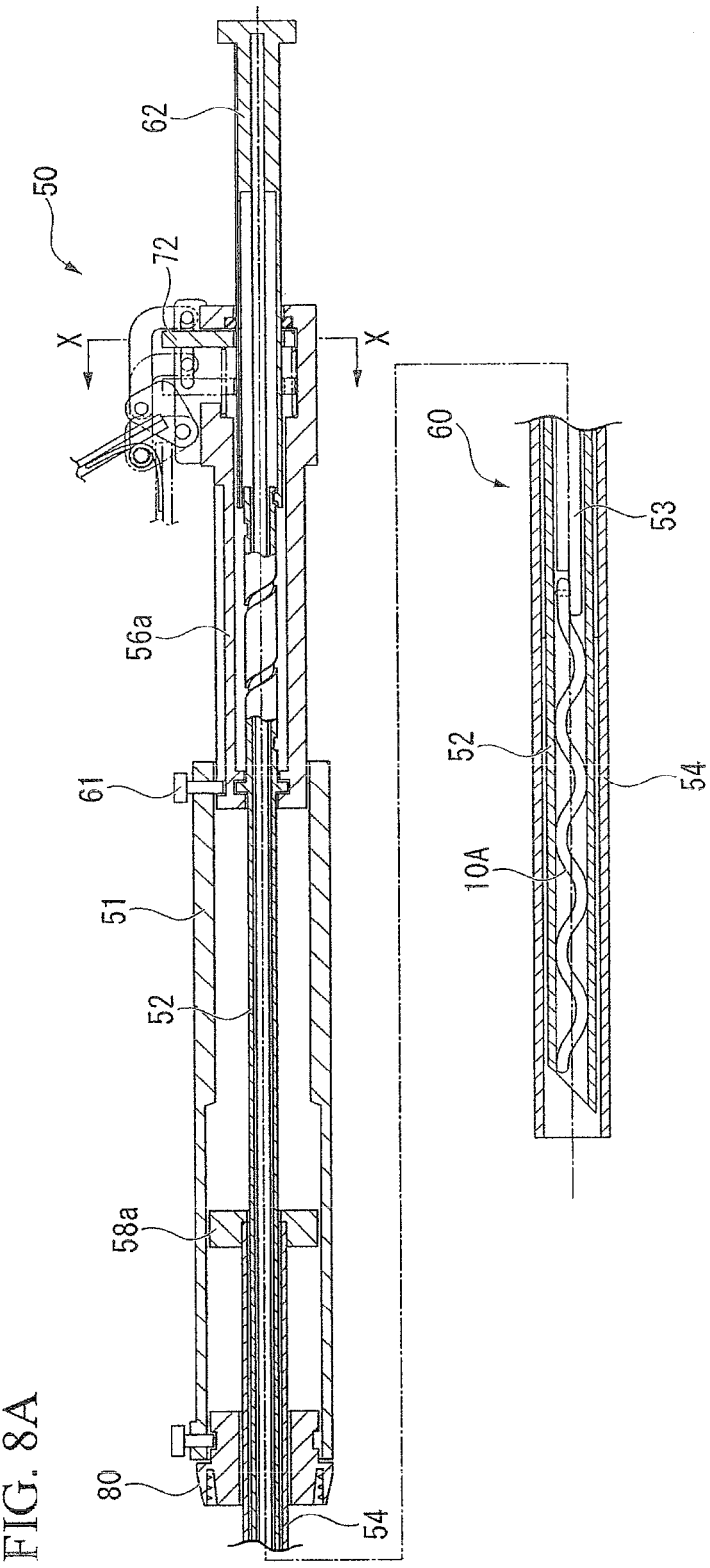
FIG. 8A is a view showing the operation when the tissue fastening tool and the applicator are used.
FIG. 8B is a sectional view in a line X-X of FIG. 8A.

As shown in FIG. 8A, prior to the procedure, the operator operates the first shaft 56a of the applicator 50 to retract the needle tube 52 with respect to the main body 51, and operates the second shaft 62 to retract the stylet 53 with respect to the main body 51. Moreover, the operator operates the ring member 58a to retract the sheath 54 with respect to the main body 51. In this state, the needle tube 52 with the tissue fastening tool 10A inserted thereinto is pulled into the sheath 54.

The operator inserts and advances the insertion section 60 of the applicator 50 into an operating channel of the endoscope 2, and engages the mouthpiece 80 with the forceps plug 8 of the endoscope to fix the applicator 50 to the endoscope 2. Thereby, the distal end of the insertion section 60 is made to project from the distal end of the insertion section 4 of the endoscope 2. Then, the direction of the projecting insertion portion 60 is adjusted by the standing base 7.

Figure 9:
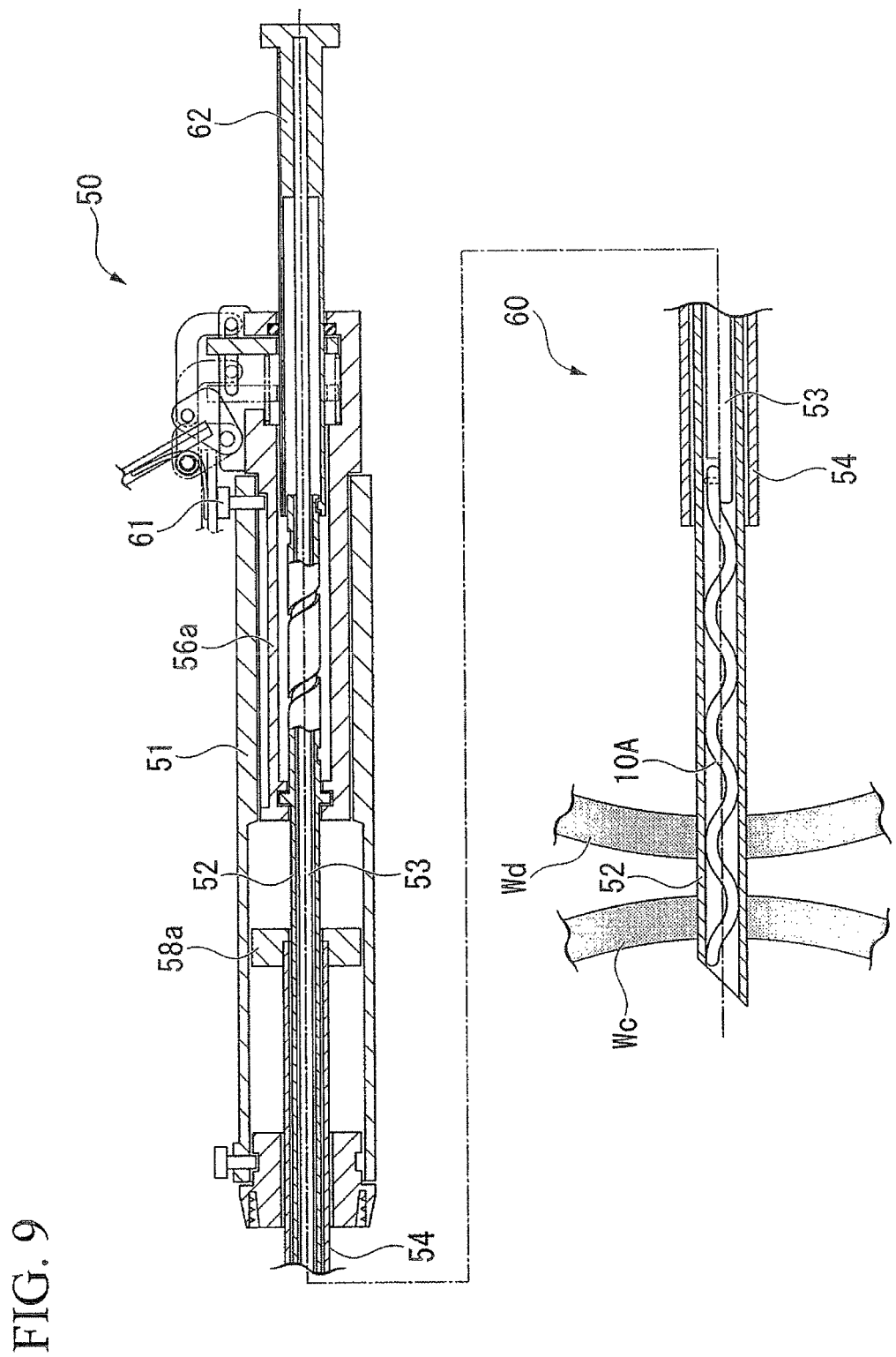
FIGS. 9 to 11 are views showing the operation when the tissue fastening tool and the applicator are used.

The common biliary duct Cb is scanned using the ultrasonic device 6 provided in the endoscope 2 over the duodenum Dd, and the position in which the needle tube 52 is to pierce the common biliary duct Cb is determined. Then, as shown in FIG. 9, the first shaft 56a is pushed into the main body 51 by loosening the external thread 61 and the distal end of the needle tube 52 is made to project from the distal end of the sheath 54. Thereby, the sharp distal end of the needle tube 52 pierces the intestinal wall Wd of the duodenum Dd from the inside toward the outside, and subsequently, pierces the duct wall Wc of the common biliary duct Cb from the outside toward the inside. Then, the operator tightens the external thread 61 to fix the first shaft 56a to the main body 51.

Figure 10:
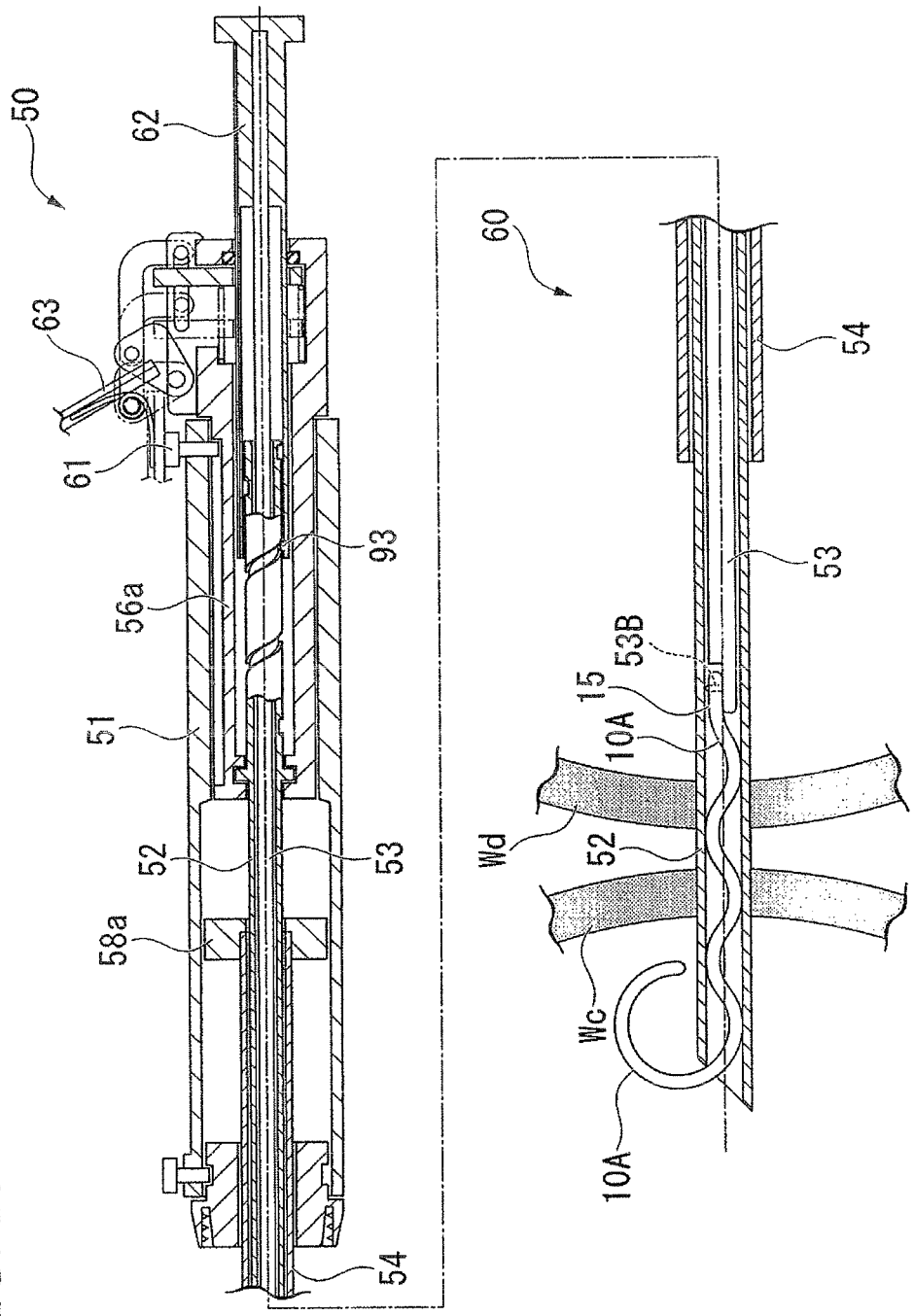

As shown in FIG. 10, the operator operates the lever 63 to push the second shaft 62 into the first shaft 56a by a predetermined amount. For example, the operator operates the lever 63 a predetermined number of times. Thereby, the stylet 53 changes its position relative to the needle tube 52, and the second tissue fixing section 12 of the tissue fastening tool 10A are pushed out of the distal end of the needle tube 52. At this time, the projection 93 provided on the second shaft 62 moves along the spiral groove 92 of the needle tube 52 in conjunction with the advance of the second shaft 62. On the other hand, the rotation of the second shaft 62 is regulated as the projection 95 of the plate member 72 is engaged with the longitudinal groove 94 formed at the outer periphery of the second shaft. As a result, the needle tube 52 rotates in conjunction with the advance of the second shaft 62. At this time, since the tissue fastening tool 10A and the stylet 53 are integrated as the projection 53B is engaged with the through hole 15B of the end coil portion 15, the advance and retract, and rotation of the stylet are suitably transmitted to the tissue fastening tool 10A.

Since the rotational direction of the needle tube 52, as seen from the proximal end of the main body 51, is set to be opposite to the winding direction of the tissue fastening tool 10A pushed out of the distal end of the needle tube 52, the second tissue fixing section 12 that is pushed out of the needle tube 52 is quickly returned to its original coil shape without being distorted (this will be described later) and is hooked onto the inside of the duct wall Wc of the common biliary duct Cb.

The first shaft 56a is pulled out slightly from the main body 51 by loosening the external thread 61, and the protruding length of the needle tube 52 from the distal end of the sheath 54 is reduced. Then, the external thread 61 is tightened so as to fix the first shaft 56a to the main body 51. Thereby, the distal end of the needle tube 52 is separated slightly from the inner surface of the intestinal wall Wd of the duodenum Dd.

Figure 11:
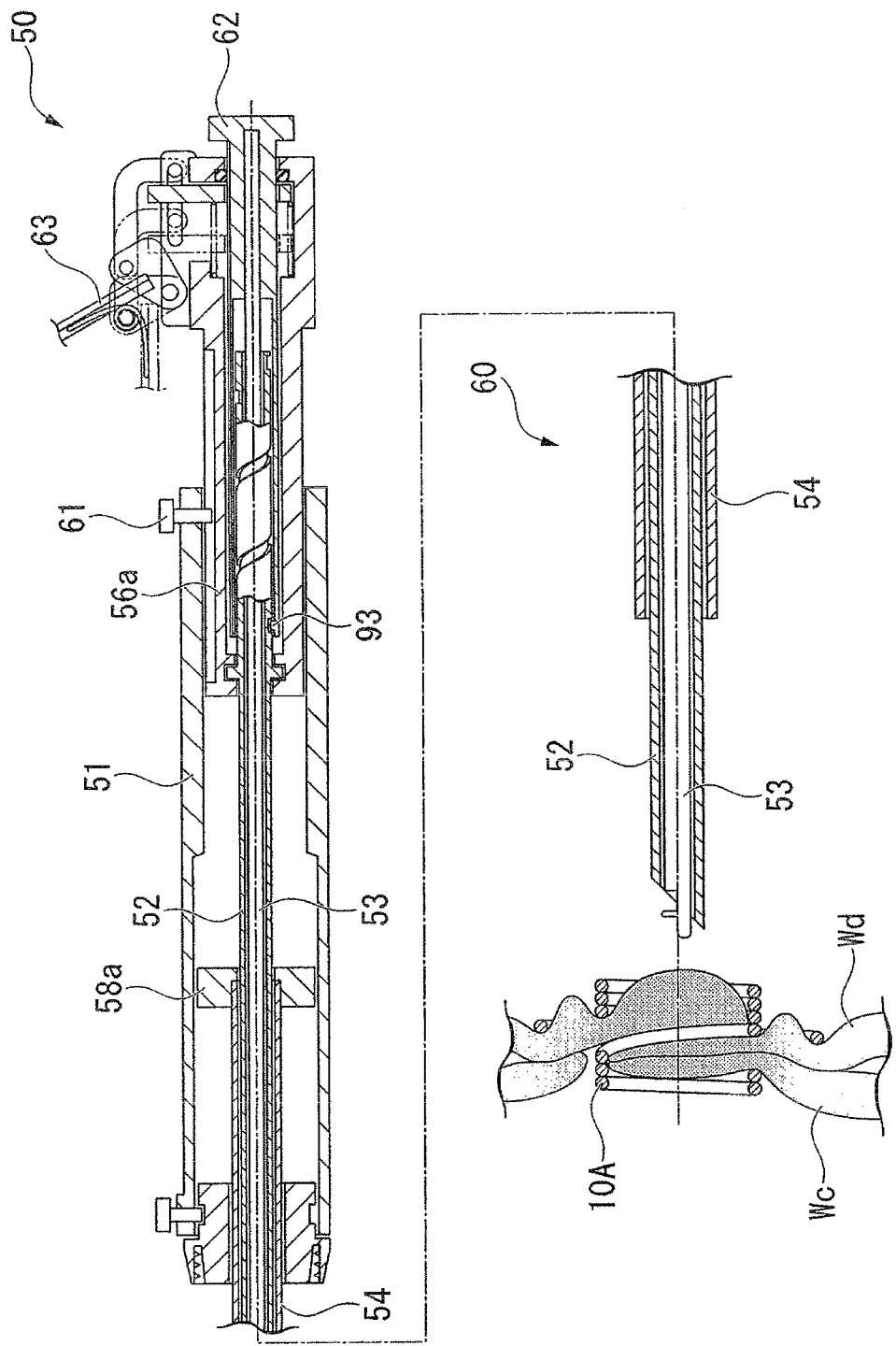

As shown in FIG. 11, the lever 63 is operated to push the second shaft 62 into the first shaft 56a by a predetermined amount. For example, the lever 63 is operated a predetermined number of times. Thereby, the stylet 53 changes its position relative to the needle tube 52, and the first tissue fixing section 11 of the tissue fastening tool 10A is pushed out of the distal end of the needle tube 52. At this time, similarly to when the second tissue fixing section 12 is pushed out, the needle tube 52 rotates in the opposite direction to the coil winding direction of the tissue fastening tool 10A. As a result, if the first tissue fixing section 11 is pushed out of the needle tube 52, the first tissue fixing section 11 quickly returns to its original coil shape without being distorted (this will also be described later) and is hooked onto the inside of the intestinal wall Wd of the duodenum Dd.

Next, the behavior of the tissue fastening tool 10A which is pushed out of the distal end of the needle tube 52 in the above-mentioned procedure will be described in detail.

First, the tissue fastening tool 10A is pushed out such that only the second tissue fixing section 12 projects from the distal end of the needle tube 52 which has passed through the intestinal wall Wd of the duodenum Dd and the duct wall We of the common biliary duct Cb. The second tissue fixing section 12 gradually returns to its original coil shape and is hooked onto the duct wall We of the common biliary duct Cb while being pushed out of the distal end of the needle tube 52.

Figure 12A:
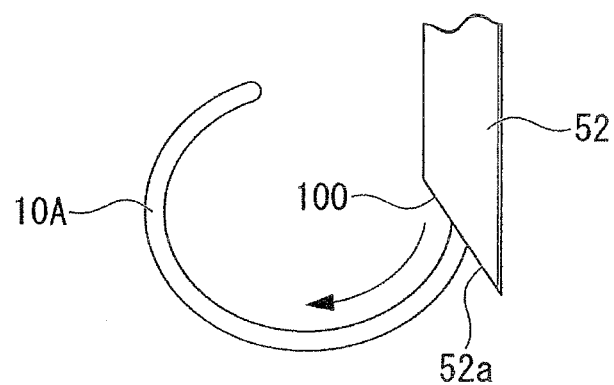
FIGS. 12A and 12B are views showing the operation when the tissue fastening tool is pushed out of a needle tube of the applicator.
Figure 12B:
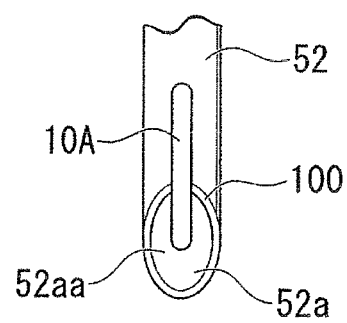

The tissue fastening tool 10A housed in the needle tube 52 in the extended state tends to return to the original shape by its elastic force outside the needle tube 52. As a result, when the tissue fastening tool is pushed out of the distal end of the needle tube 52, as shown in FIGS. 12A and 12B, it is pushed out while the inner surface of the loop of the fastening tool 10A is directed to an opening 100 of the distal end of the needle tube 52 that is closest to its root. When the distal end of the needle tube 52 has a slant opening 52a slanting like an injection needle, the tissue fastening tool 10A is pushed out of the portion of the slant opening 52a that is closest to its root, and tends to return to its original shape while being located on the plane substantially perpendicular to the slant opening 52aa.

Accordingly, if the needle tube tool 52 is rotated while the tissue fastening tool 10A is pushed out of the slant opening 52a of the needle tube 52, the tissue fastening tool 10A rotates integrally with the needle tube 52.

When the tissue fastening tool 10A is pushed out of the needle tube 52, in the case where the tissue fastening tool 10A does not touch the duct wall We of the surrounding common biliary duct, the tissue fastening tool 10A returns correctly to its original shape. However, in a case where the tissue fastening tool 10A touches the duct wall We of the surrounding common biliary duct or the like, the tissue fastening tool 10A may not return to its original shape.

This phenomenon will be described taking the case where the tissue fastening tool 10A is a right-handed winding (Z winding) coil as an example. If the tissue fastening tool 10A is pushed further out of the needle tube 52 from the state shown in FIGS. 12A and 12B, the tissue fastening tool 10A normally returns to a right-handed winding coil as shown in FIG. 13A. However, when the tissue fastening tool 10A touches the duct wall We of the common biliary duct as shown in FIG. 13B, there is the possibility that the tissue fastening tool 10A is pushed by the duct wall We of the common biliary duct and is formed into a left-handed winding coil (S winding) opposite to its original shape.

In order to prevent this, the tissue fastening tool 10A may be pushed out of the needle tube 52 while being rotated integrally with the needle tube 52 so that the needle tube 52 is rotated in the direction opposite to the winding direction of the tissue fastening tool 10A as shown in FIG. 13C, i.e., to the left as seen from its proximal end if the tissue fastening tool 10A is a right-handed winding coil. Thereby, the tissue fastening tool 10A rotates left along with the needle tube 52, and pushes the duct wall We of the common biliary duct. Consequently, the tissue fastening tool 10A returns to its original right-handed winding coil.

In the applicator 50 of the present embodiment, the shape of the spiral groove 92 is set so that the rotational direction of the needle tube 52 rotates in a counterclockwise direction toward the distal side that is opposite to the winding direction of the tissue fastening tool 10A. Accordingly, the needle tube 52 and the stylet 53 rotates in the counterclockwise direction when the tissue fastening tool 10A is fed out. Moreover, since the tissue fastening tool 10A and the stylet 53 are engaged with each other, the rotation of the stylet 53 is transmitted to the tissue fastening tool 10A well, and the tissue fastening tool 10A is fed out of the needle tube 52 while being reliably rotated. By these operations, as shown in FIG. 13D, the tissue fastening tool 10A pushed out of the needle tube 52 returns to its original right-handed winding coil shape well, and entanglement or decrease in the fastening force of a tissue that is caused by the change of the winding direction is prevented.

After the second tissue fixing section 12 of the tissue fastening tool 10A is pushed out of the needle tube 52 inside the common biliary duct Cb, the first tissue fixing section 11 is pushed out of the distal end of the needle tube 52 which is extracted from the intestinal wall Wd of the duodenum Dd and the duct wall Wc of the common biliary duct Cb. Even at this time, since the needle tube 52 is rotated while the tissue fastening tool 10A is pushed out of the slant opening 52a of the needle tube 52, the portion of the basic loop of the tissue fastening tool 10A is smoothly indwelled.

Figure 14:
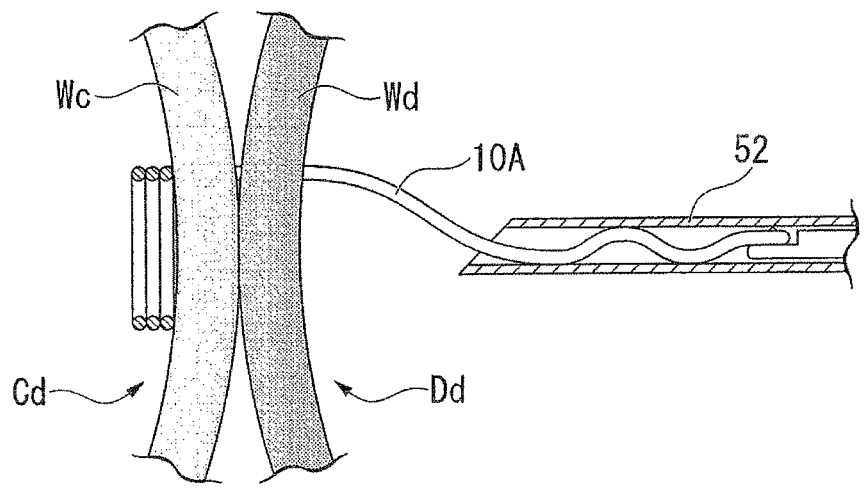
FIGS. 14 to 16 are views showing a state where a trouble has occurred when the tissue fastening tool is indwelled.
Figure 15:
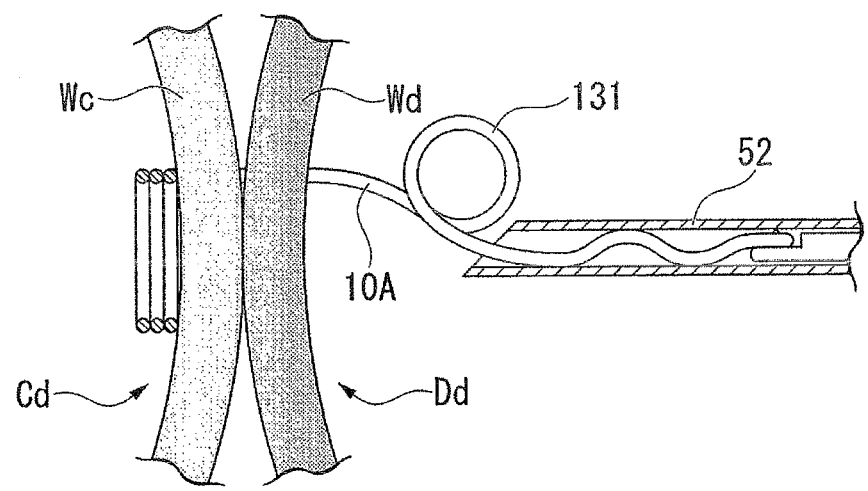
Figure 16:
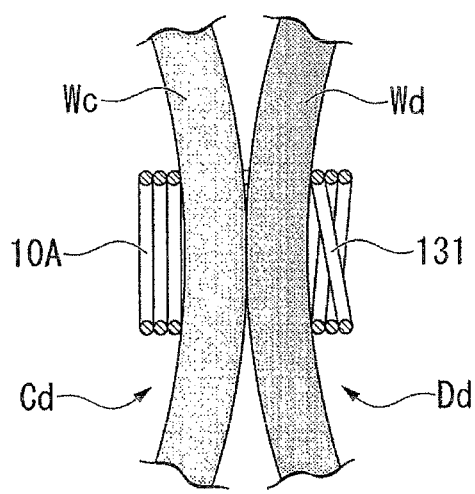
Figure 17:
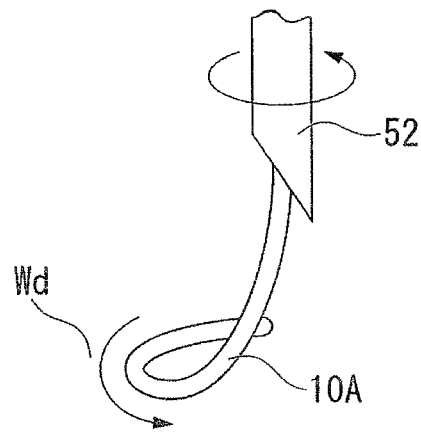
FIGS. 17 to 21 are views showing the operation of the tissue fastening tool and the needle tube for suitably indwelling the tissue fastening tool.
Figure 18:
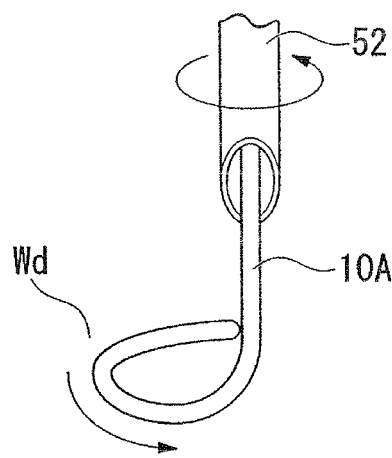
Figure 19:
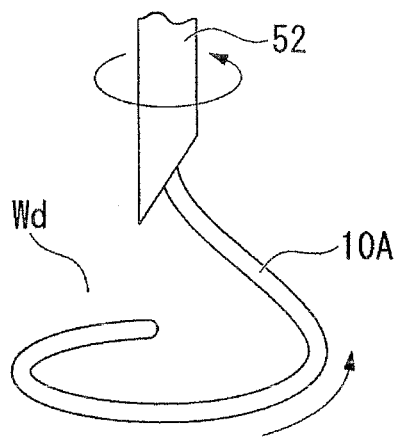
Figure 20:
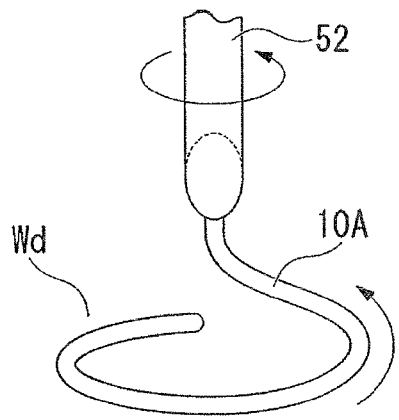

FIGS. 14 to 16 are explanatory views of a problem when the tissue fastening tool 10A is hooked onto the first biological tissue after the tissue fastening tool 10A is hooked onto the second biological tissue. As shown in these drawings, when the tissue fastening tool 10A is hooked onto, for example, the intestinal wall Wd of the duodenum Dd that is the first biological tissue after the tissue fastening tool 10A is hooked onto, for example, the duct wall Wc of the common biliary duct Cb that is the second biological tissue, as shown in FIG. 15, a twisted portion 131 is generated by the force that the tissue fastening tool 10A returns to its original coil shape. Finally, as shown in FIG. 16, there is a possibility that the tissue fastening tool 10A may be indwelled in an entangled state with the twisted portion 131 as the starting point.

In the tissue fastening tool 10A and applicator 50 of the present embodiment, the above entanglement is suitably prevented. Hereinafter, a detailed description will be given.

The returning movement of the tissue fastening tool 10A to its original coil shape when being indwelled on the intestinal wall Wd of the duodenum Dd is also the rotational movement of the tissue fastening tool on the intestinal wall Wd as shown in FIGS. 17 to 21. Thus, if the movement of the tissue fastening tool 10A and the rotation of the needle tube 52 are synchronized with each other, the tissue fastening tool 10A can be smoothly indwelled.

Figure 21:
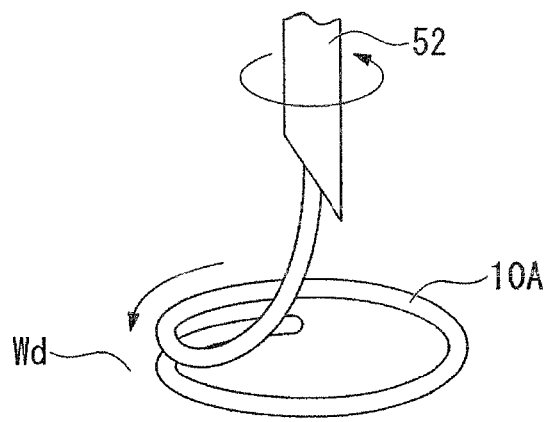

Specifically, when the tissue fastening tool 10A is a right-handed winding coil, the metal wire rod 10 that constitutes the tissue fastening tool 10A extends in a counterclockwise direction toward the proximal side, as seen from the proximal side. Accordingly, as shown in FIGS. 17 to 21, the needle tube 52 is rotated in a counterclockwise direction as seen from the proximal side, whereby the rear end of the tissue fastening tool 10A is smoothly fed out of the needle tube 52, and the tissue fastening tool returns to a right-handed winding loop shape as shown in FIG. 21 without causing torsion or entanglement. Moreover, when the tissue fastening tool 10A is pushed out of the distal end of the needle tube 52 by about a length equivalent to one loop winding, the rotating mechanism 96 is set up that the needle tube 52 substantially makes one rotation. Thus, when the needle tube 52 makes one rotation, the loop of the tissue fastening tool 10A returns one winding outside the needle tube 52. As a result, the rotational operation of the needle tube 52 and indwelling operation of the tissue fastening tool 10A are synchronized at a high level, and indwelling becomes easier.

Figure 22:
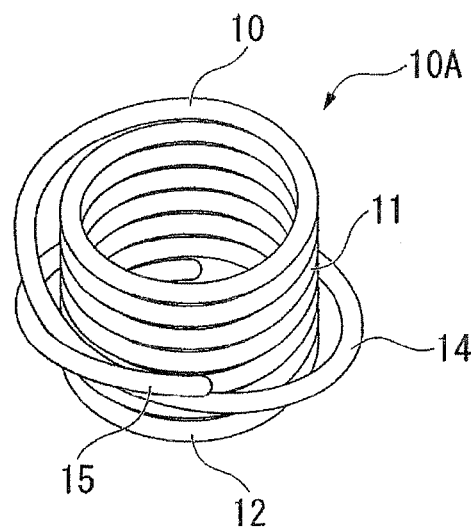
FIG. 22 is a view showing a state where the outer peripheral spring has been ridden on the end coil portion in the tissue fastening tool.

After the indwelling of the first tissue fixing section 11 end, the spring portion 14 and the end coil portion 15 are then fed out of the needle tube 52. Even at this time, since the needle tube 52 is rotated in the counterclockwise direction as seen from its proximal end as described above, each part of the outer peripheral spring portion 13 is smoothly fed out, and returns to a loop shape accommodated in the needle tube 52. Since the loop diameter of the end coil portion 15 is larger than the loop diameter of the spring portion 14, as shown in FIG. 22, there is no possibility that the end coil portion 15 rides on the spring portion 14, and the pressing-down ability of the intestinal wall Wd as will described later decreases.

Figure 23:
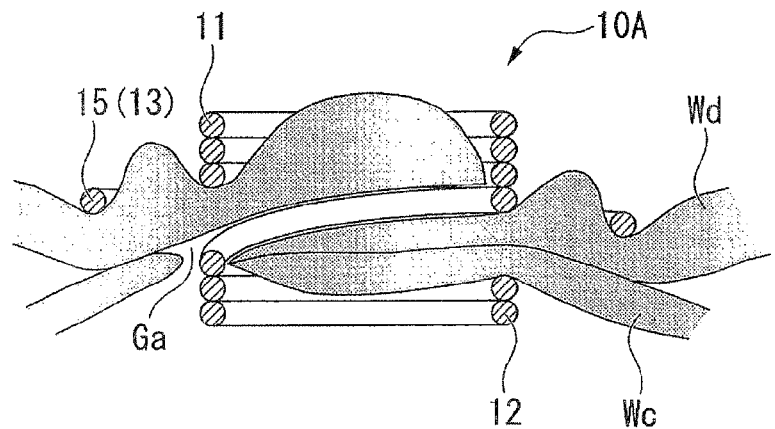
FIG. 23 is a view showing a state where the tissue fastening tool has been indwelled in a tissue.

If the whole tissue fastening tool 10A is pushed out of the needle tube 52, the engagement between the through hole 15B at the end 15A of the end coil portion 15 and the projection 53B of the stylet 53 is automatically released, and the tissue fastening tool 10A is separated from the stylet 53. As shown in FIGS. 11 and 23, indwelling of the tissue fastening tool 10A is completed in this way. By the indwelling of the tissue fastening tool 10A, the first tissue fixing section 11 and the second tissue fixing section 12 fasten the intestinal wall Wd of the duodenum and the duct wall We of the common biliary duct so as to bring the walls into close contact with each other, and the outer peripheral spring portion 13 pushes the intestinal wall Wd against the duct wall We.

Figure 24A:
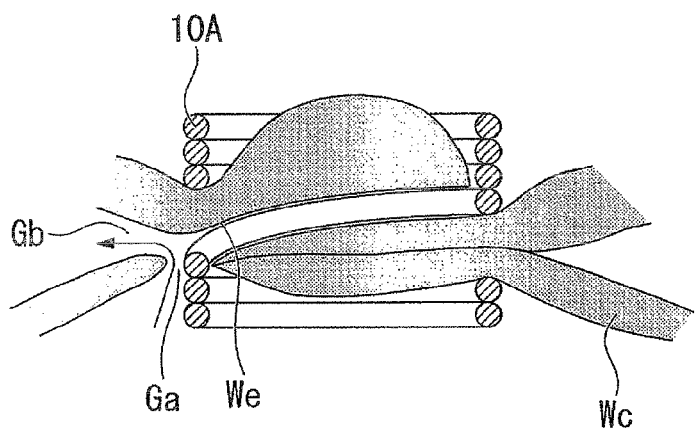
FIG. 24A is a view illustrating a problem when the tissue fastening tool has been indwelled without the outer peripheral spring.
Figure 24B:
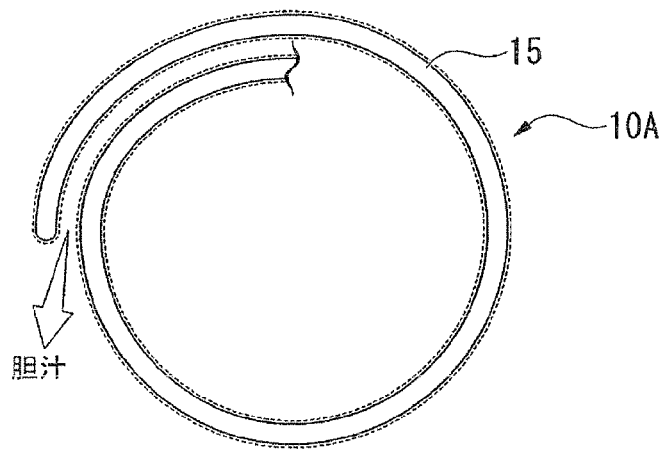
FIG. 24B is a view illustrating a problem when the tissue fastening tool in which the shape of the outer peripheral spring is not suitable has been indwelled.

When the tissue fastening tool 10A is not provided with the outer peripheral spring portion 13, as shown in FIG. 24A, the gap Ga is formed between the hole We formed in the duct wall Wc of the common biliary duct when puncture is made by the needle tube 52, and the metal wire rod 10 disposed to pass through the hole We, the phenomenon that a body fluid, such as bile, flows out through the gap Ga, and leaks into the body cavity through the gap Gb between the intestinal wall Wd of the duodenum and the duct wall Wc of the common biliary duct occurs. When the body fluid is bile, there is a possibility that biliary peritonitis will be caused. Additionally, even if there is the outer peripheral spring portion, if the end coil portion 15 that is brought into close contact with the intestinal wall Wd does not form a closed loop, as shown in FIG. 24B, there is a possibility that a gap may be made at the intestinal wall Wd to be suppressed, and leakage of body fluid may occur.

Figure 25A:
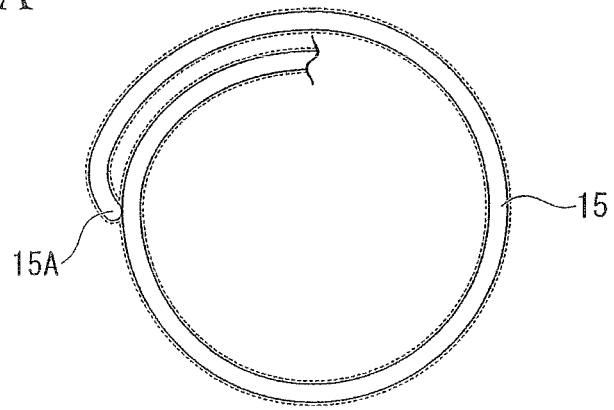
FIGS. 25A and 25B are views showing the shape of the end coil portion in plan view.

In the tissue fastening tool 10A of the present embodiment, the end 15A of the end coil portion 15 comes into contact with the portion of the end coil portion 15 that has rotated once or more. Thus, as shown in FIG. 25A, the closed loop is formed by the end coil portion 15. As a result, since the intestinal wall Wd outside the basic loop L1 is pushed in a closed annular shape, the tissue fastening tool 10A is indwelled without forming the gap Gb, and even if a body fluid, such as bile, has leaked out through the gap Ga, this body fluid does not leak to a body cavity from the gap between the intestinal wall Wd of the duodenum and the duct wall Wc of the common biliary duct.

Figure 26A:
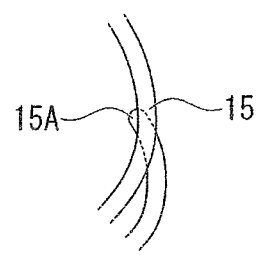
FIGS. 26A and 26B are views showing another aspect of the end coil portion.
Figure 26B:
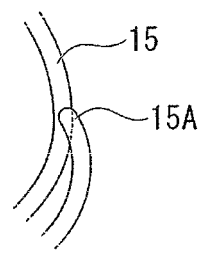
Figure 27:
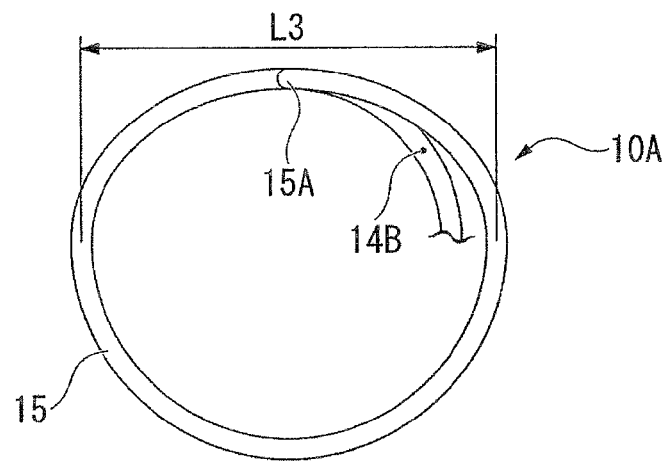
FIG. 27 is a view showing still another aspect of the end coil portion.

The end coil portion 15 has only to form a closed loop, and the aspect of contact between the end 15A and other parts of the end coil portion 15 is not particularly limited. Accordingly, as shown in FIG. 26A, the end 15A may hide under other parts of the end coil portion 15, and as shown in FIG. 26B, the end 15A may ride on other parts of the end coil portion 15. Moreover, as shown in FIG. 27, the end 14B of the outer peripheral spring that becomes a boundary point between the spring portion 14 and the end coil portion 15 may be located inside the third loop L3 that the end coil portion 15 forms. Additionally, when the end coil portion 15 forms a loop of one rotation or more, the part that has extended by one rotation or more may completely overlap other end coil portions in the same radial direction as the third loop L3.

Figure 25B:
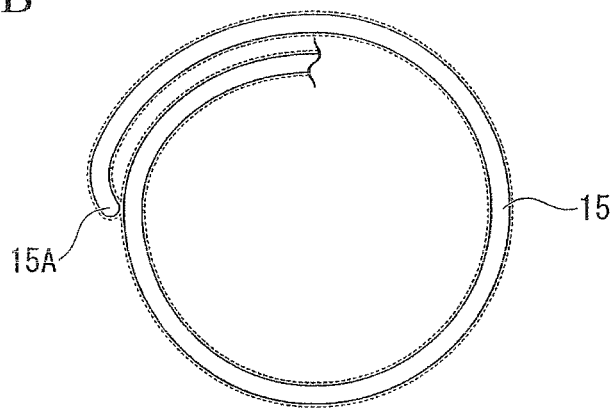

In addition, the end 15A does not need to surely touch the end coil portion 15, and if the gap between the end 15A and other parts of the end coil portion 15 is sufficiently small as shown in FIG. 25B, the whole end coil portion 15 can suppress the intestinal wall Wd without a gap. Even in such a case, the end coil portion 15 can be said to form a substantially closed loop, and there is no problem. Moreover, when the tissue fastening tool 10A is not indwelled, the shape of the outer peripheral spring portion 13 may be set so that the end 15A and other parts of the end coil portion 15 do not contact each other, but are indwelled in a tissue to form a substantially closed loop when the end coil portion 15 abuts the first biological tissue.

After the indwelling of the tissue fastening tool 10A, an operator accommodates the needle tube 52 of the applicator 50 within the sheath 54, and extracts the applicator 50 and the endoscope 2 out of the body to complete the procedure. The wall Wd of the duodenum and the duct wall We of the common biliary duct that are located within the basic loop L1 are fastened by the first tissue fixing section 11 and the second tissue fixing section 12, whereby the flow of blood is obstructed, and eventually, a pressure necrosis is caused. Simultaneously with this, the intestinal wall Wd and the duct wall Wc coalesce and join together around the basic loop L1.

The necrotized tissue and the tissue fastening tool 10A will fall off of the indwelled part. At this time, the first tissue fixing section 11 and the second tissue fixing section 12 are always biased toward the inner cavity of the duodenum by the outer peripheral spring portion 13. Thus, when the tissue fastening tool 10A drops out of other tissues, the tissue fastening tool necessarily drops out toward the inner cavity of the duodenum, and the tissue fastening tool 10A is quickly excreted through the small intestine and the large intestine to the outside of the body. Since the end 15A of the end coil portion 15 that has been engaged with the stylet 53 extends toward other parts of the end coil portion 5, the end do not wound other tissues within the body during an excretion process.

Figure 28:
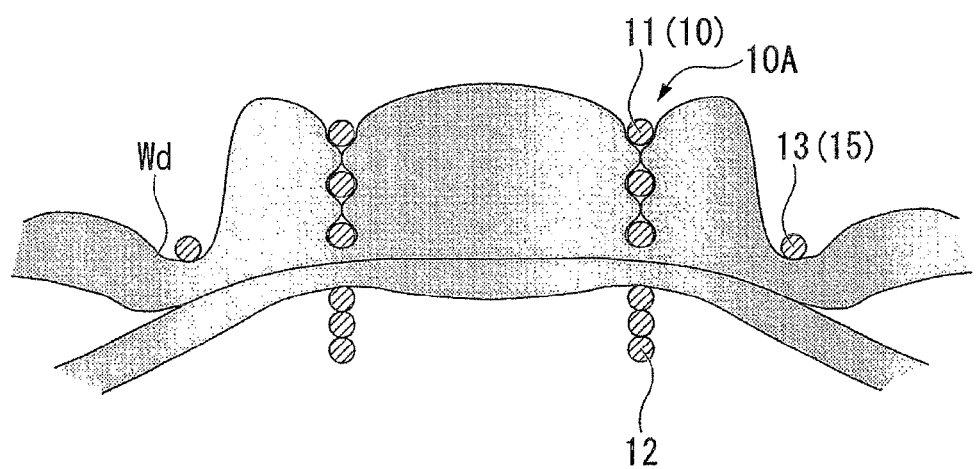
FIG. 28 is a view showing a state where the fastening force of the tissue fastening tool is not enough.

Although the outer peripheral spring portion 13 pushes the intestinal wall Wd of the duodenum against the duct wall Wc of the common biliary duct, the reaction force at that time also serves as a force that pulls the first tissue fixing section 11 apart from the intestinal wall Wd. Accordingly, if the initial tension of the first tissue fixing section 11 is smaller than the biasing force of the outer peripheral spring portion 13, as shown in FIG. 28, the fastening force between the first tissue fixing section 11 and the second tissue fixing section 12 becomes weaker, and a gap is formed between the metal wire rods 10 of the first tissue fixing section 11.

If the force that fastens the intestinal wall Wd and the duct wall We becomes weak in this way, the flow of blood of the intestinal wall Wd and the duct wall Wc cannot be sufficiently obstructed. Additionally, if the gap is formed between the metal wire rods 10 that constitute the first tissue fixing section 1, the flow of blood occurs between a tissue within the basic loop L1 and its outside tissue. Therefore, the tissue within the basic loop L1 will not necrose. Accordingly, drop-out does not occur, and a subsequent fistulous opening cannot be formed.

In the tissue fastening tool 10A of the present embodiment, the initial tension of the first tissue fixing section 11 is set to such a degree that the first tissue fixing section 11 is not pulled apart from the intestinal wall Wd as shown in FIG. 23, and a gap is not formed between the metal wire rods 10 even when the tissue fastening tool receives the reaction force when the distal end of the outer peripheral spring portion 13 has pressed down the intestinal wall Wd when the tissue fastening tool 10A is indwelled within the body. As a result, at the time of indwelling, a gap is not formed and a close contact state can be maintained, between the metal wire rods 10 of the first tissue fixing section 11. Therefore, the flow of blood to the tissue within the basic loop L1 is suitably intercepted, and the tissue necroses reliably. Thereafter, the tissue fastening tool 10A and the necrotized tissue drop out, and a fistulous opening that connects the intestinal wall Wd of the duodenum and the duct wall We of the common biliary duct is formed.

According to the tissue fastening tool 10A of the present embodiment, the first tissue fixing section 11 and the second tissue fixing section 12 can suitably fasten the first biological tissue and the second biological tissue, can necrose portions of both tissues while coalescing other portions, and can easily form a fistulous opening that allows the first biological tissue and the second biological tissue to communicate with each other.

Additionally, in the outer peripheral spring portion 13, the second loop L2 that the spring portion 14 forms is larger than the basic loop L1 that the first tissue fixing section 11 and the second tissue fixing section 12 form, the third loop L3 that the end coil portion 15 forms is set to be larger than the second loop L2, and these loops are set so as not to overlap each other in the radial direction of the basic loop L1.

Accordingly, torsion or entanglement between the metal wire rods between the loops does not occur, and each part can reliably exhibit a predetermined fastening force or biasing force and safely use.

Moreover, since the end 15A of the end coil portion 15 has extended toward other parts of the end coil portion 15, the end coil portion 15 forms a closed loop to suitably prevent the leakage of a body fluid as described above, the end 15A is not exposed, and other tissues are not harmed while the tissue fastening tool 10A is discharged to the outside of the body.

Additionally, according to the applicator 50 of the present embodiment, the tissue fastening tool 10A and the stylet 53 are engaged with each other in a state where the tissue fastening tool 10A is accommodated in the needle tube 52. Thus, the advance/retreat and rotation of the stylet 53 are suitably transmitted to the tissue fastening tool 10A as described above.

When the stylet 53 and the tissue fastening tool 10A are not engaged with each other, the tissue fastening tool 10A may deviate to the outside of the needle tube 52 to the unintended part by a restoring force to return to an original shape outside the needle tube 52, and the tissue fastening tool 10A may not return to the same shape as before the accommodation. If the stylet 53 and the tissue fastening tool 10A are connected together, unintended deviation of such a tissue fastening tool 10A is suppressed, and the tissue fastening tool 10A is reliably restored to the same shape as before the accommodation, and is indwelled.

Additionally, if the tissue fastening tool 10A and the stylet 53 are engageable with each other, the tissue fastening tool 10A can be easily accommodated within the needle tube 52 by making the stylet 53 retreats into the needle tube 52 while rotating the stylet.

Moreover, since the tissue fastening tool 10A and the stylet 53 are automatically disengaged with each other outside the needle tube 52, an operator can indwell the tissue fastening tool 10A without requiring a special operation for the disengagement.

Figure 29A:
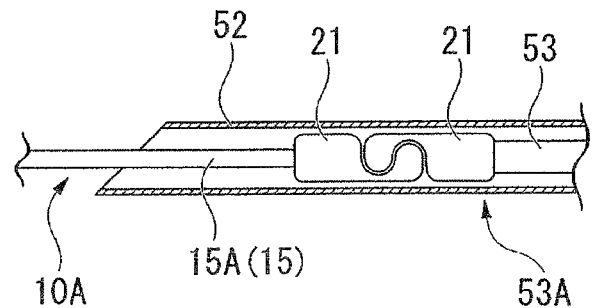
FIGS. 29A and 29B are views showing a connection aspect between the tissue fastening tool and a stylet in a modification of the present embodiment.
Figure 29B:
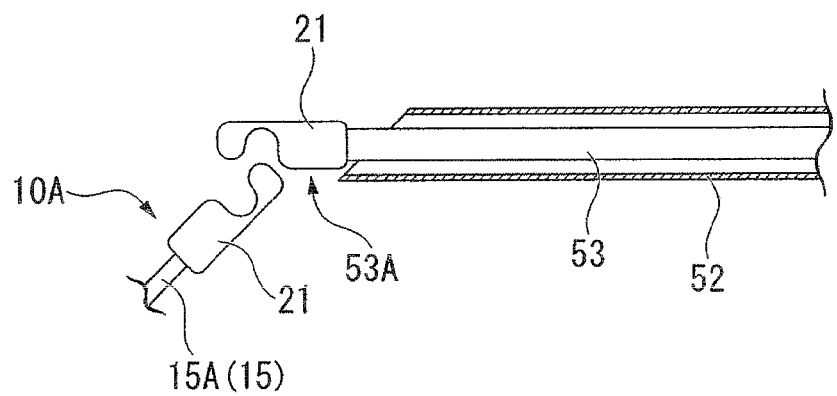

The joining aspect between the tissue fastening tool 10A and the stylet 53 is not limited to the above-mentioned ones, and various aspects can be adopted. For example, like a modification shown in FIGS. 29A and 29B, the distal end 53A of the stylet 53 and the end 15A the end coil portion 15 of the tissue fastening tool 10A may be provided with hooks 21 that are engageable with each other, and both may be disengageably connected together within the needle tube 52. In providing the hooks 21, processing, such as cutting may be performed on the distal end 53A and the end 15A, and members that have a shape like the hooks 21 may be attached to the distal end 53A and the end 15A by caulking, welding, etc. Additionally, although the example in which the distal end 53A and the end 15A has the same hook 21 has been described in the above modification, hooks with different shapes may be attached if they are engageable with each other. It is noted that, if the same hook is used, the number of parts can be reduced, and manufacture efficiency can be improved.

Figure 30A:
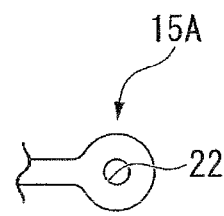
FIGS. 30A and 30B are views showing an end of the tissue fastening tool in the modification of the present embodiment.
Figure 30B:
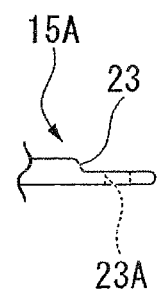
Figure 31:
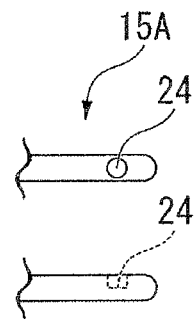
FIG. 31 is a view showing an end of the tissue fastening tool in the modification of the present embodiment.

Additionally, even when the end 15A is provided with a through hole, like the modification shown in FIG. 30A, the through hole 22 may be formed by extending the end 15A, and like the modification shown in FIG. 30B, a stepped portion 23 may be provided by cutting or the like and the stepped portion 23 may be formed with a through hole 23A. Moreover, like the modification shown in FIG. 31, a bottomed recess 24 may be provided instead of a through hole.

Figure 32A:
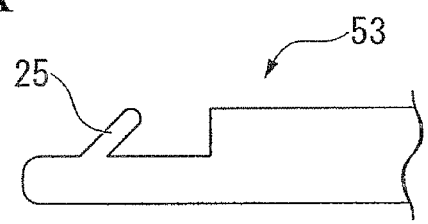
FIGS. 32A and 32B are views showing another connection aspect between the tissue fastening tool and the stylet.
Figure 32B:
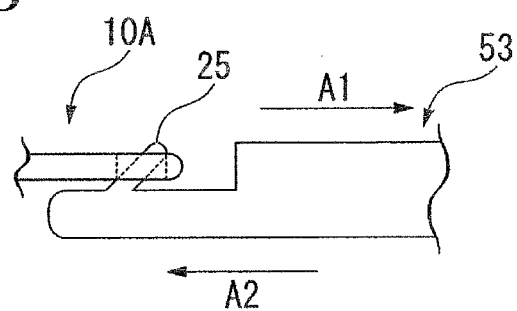
Figure 33:
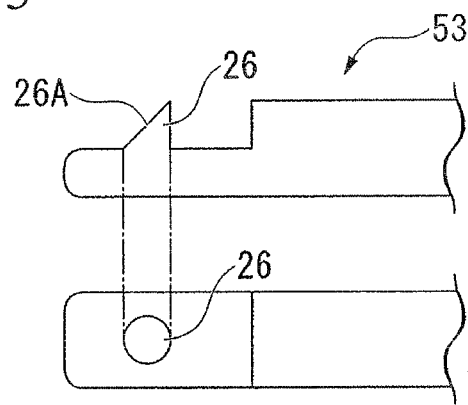
FIG. 33 is a view showing an end of the stylet in the modification of the present embodiment.

Additionally, a distal end of a projection provided on the stylet 53 may be formed so as to incline toward the proximal side like a projection 25 shown in FIG. 32A. Since this makes it hard to release the engagement with the tissue fastening tool 10A when the stylet 53 is moved in the direction of an arrow A1 shown in FIG. 32B, the tissue fastening tool 10A is easily accommodated within the needle tube 52 at the time of manufacture or the like. On the other hand, when the stylet 53 is moved in the direction of an arrow A2, the engagement between both are easily released and smooth operation is allowed at the time of indwelling. Even in this case, the engagement can be suitably prevented from being released within the needle tube 52 by suitably setting the dimensions of the stylet 53 and the tissue fastening tool 10A with respect to the needle tube 52, thereby making the movable width small in the cross-sectional direction of the stylet 53 or the tissue fastening tool 10A within the needle tube 52. The above-described effects, like the modification shown in FIG. 33, can be similarly obtained even when a projection 26 is formed so as to have a slope 26A that makes an acute angle with the axis of the stylet 53 on the proximal side.

Figure 34:
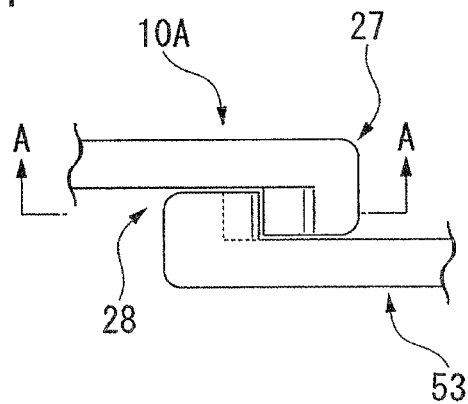
FIGS. 34 to 36 are views showing another connection aspect between the tissue fastening tool and the stylet.
Figure 35:
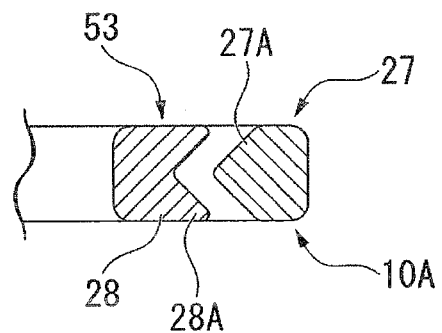
Figure 36:
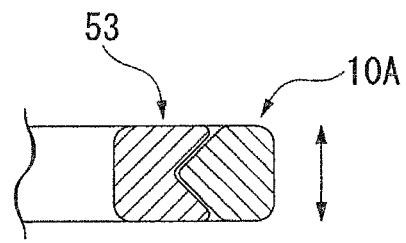
Figure 37:
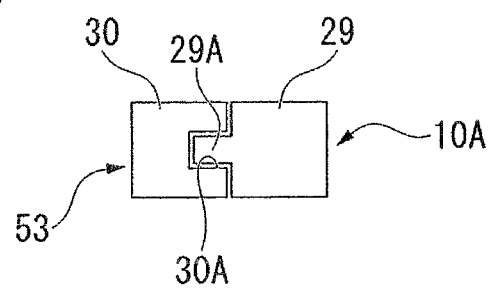
FIG. 37 is a view showing another connection aspect between the tissue fastening tool and the stylet.

Moreover, like the modification shown in FIGS. 34 and 35 (a sectional view in the line A-A of FIG. 34), the tissue fastening tool 10A and the stylet 53 are respectively formed with an engaging portion 27 and an engaged portion 28 that are disengageable with each other and respectively have regulating portions 27A and 28A that regulate the relative movement in the direction along the width. Since this regulates movement in the width direction (direction indicated by an arrow in FIG. 36) of the tissue fastening tool 10A and the stylet 53 as shown in FIG. 36, the tissue fastening tool 10A is engaged with the stylet 53 and easily accommodated within the needle tube 52 at the time of manufacture or the like. There is no particular limitation to the shape of the regulating portions if they can regulate movement in the width direction of the tissue fastening tool 10A and the stylet 53. For example, as shown in FIG. 37, an engaging portion 29 and an engaged portion 30 that respectively have a convex portion 29A and a concave portion 30A as the regulating portions may be provided in the tissue fastening tool 10A and the stylet 53, respectively.

Figure 38A:
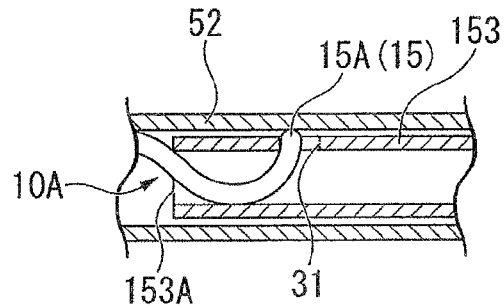
FIGS. 38A and 38B are views showing another connection aspect between the tissue fastening tool and the stylet.
Figure 38B:
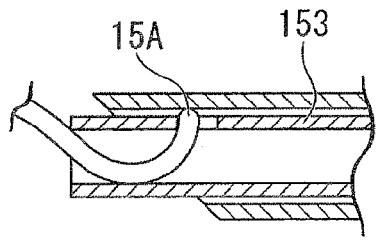
Figure 39A:
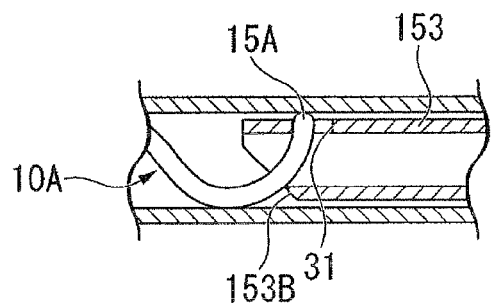
FIGS. 39A and 39B are views showing another connection aspect between the tissue fastening tool and the stylet.
Figure 39B:
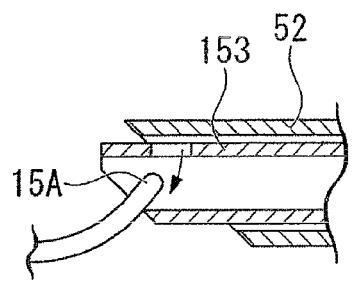

Moreover, as shown in FIG. 38A, at least the region of the stylet 153 with constant length on the distal side may be formed in a hollow shape having an inner cavity to form a through hole 31 at an outer peripheral surface thereof, and the end 15A of the end coil portion 15 of the tissue fastening tool 10A may be advanced into the inner cavity and be made to project from the through hole 31, thereby engaging the stylet 153 with the tissue fastening tool 10A. However, in this case, if an opening end face 153A of the distal end of the stylet 153 has a shape orthogonal to the axis of the stylet 153, as shown in FIG. 38B, the outer peripheral surface of the end 15A may be caught on the inner surface of the stylet 153, and its engagement may be hardly released outside the needle tube 52. Therefore, as shown in FIG. 39A, the shape of an opening end face 153B may be set so that the length of the stylet 153 may be smallest at the position that faces the through hole 31 across the axis of the stylet 153. This is not preferable because, as shown in FIG. 39B, the outer peripheral surface of the end 15A hardly strikes the inner surface of the stylet 153 when the engagement is released and the engagement is easily released outside the needle tube 52.

In addition, in the modification shown in FIGS. 38A to 39B, the end 15A of the end coil portion 15 of the tissue fastening tool 10A may be bent so as to be easily engaged with the through hole 31.

Figure 40A:
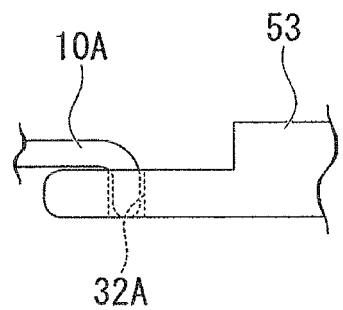
FIGS. 40A and 40B are views showing another connection aspect between the tissue fastening tool and the stylet.
Figure 40B:
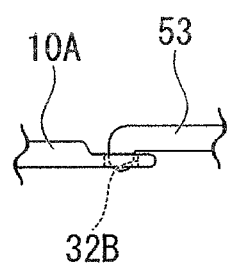

Additionally, instead of providing a projection on either the tissue fastening tool 10A or the stylet 53, one end may be bent and locked to a through hole 32A or 32B that has a larger diameter than the other wire diameter provided at the other end like the modification shown in FIGS. 40A and 40B. In this case, since the through hole with a relatively large diameter is needed in order to enable entrance of one end, the through hole 22 or the like may be provided in the tissue fastening tool 10A or the stylet 53 by the method as shown in FIG. 30A.

Although the preferable embodiments of the present invention have been described hitherto, the present invention is not limited to these embodiments. Additions, omissions, substitutions, and other modifications can be made without departing from the spirit or scope of the present invention.

In addition, the invention is not limited by the above description and is limited by only the scope of appended claims.

What is claimed is:

1. A tissue fastening tool indwelling apparatus comprising:
a long axis member in which an opening is formed at a distal end side thereof, the long axis member being provided with a lumen having a longitudinal axis and being communicated with the opening;
a stylet inserted into the lumen so as to freely move along a longitudinal axis direction in the lumen and to be rotatable around the longitudinal axis direction;
an operating section that moves the stylet to the longitudinal axis direction in the lumen and rotates the stylet around the longitudinal axis direction in the lumen;
a connecting section that is formed at a distal end of the stylet, is detachably connected to a tissue fastening tool, which is configured such that a wire wound in a coil form is arranged while being stretched, and moves along and rotates around the longitudinal axis direction in the lumen with the stylet and the tissue fastening tool depending on an operation of the operating section, and
a rotating mechanism that guides the stylet to a direction which moves the stylet toward the distal end of the long axis member relative to the long axis member and that guides the stylet in a direction which rotates the stylet around the longitudinal axis depending on an operation of the operating section, wherein
the rotating mechanism is configured to rotate the stylet in a wound direction of the tissue fastening tool in which the tissue fastening tool restores to the coil form so that compressing force of the tissue fastening tool acts in an axial direction of the tissue fastening tool when the tissue fastening tool is protruded from the long axis member.

2. The tissue fastening tool indwelling apparatus according to claim 1,
wherein the diameter of the tissue fastening tool, the dimensions of an inner cavity of a needle tube, and the dimensions of the stylet are set so that the engagement between the tissue fastening tool and the stylet is not released within the needle tube.

3. The tissue fastening tool indwelling apparatus according to claim 1,
wherein the tissue fastening tool and the stylet are connected so as to be capable of integrally advancing and retreating within a needle tube.

4. The tissue fastening tool indwelling apparatus according to claim 1,
wherein, if the rotation mechanism rotates the stylet one rotation in the opposite direction, the stylet advances inside a needle tube so that the tissue fastening tool is pushed out by a length equivalent to one coil turn.

5. The tissue fastening tool indwelling apparatus according to claim 1,
wherein the rotating mechanism rotates a needle tube in the same direction as the stylet along with the stylet.

6. The tissue fastening tool indwelling apparatus according to claim 1,
wherein one of an end of the tissue fastening tool and a distal end of the stylet is provided with an engaging portion, the other one is provided with an engaged portion that is engageable with the engaging portion and the engaged portion are engaged with each other.

7. The tissue fastening tool indwelling apparatus according to claim 6,
wherein at least one of the engaging portion and the engaged portion is formed in the connecting section, and is attached to one the end of the tissue fastening tool and the distal end of the stylet.

8. The tissue fastening tool indwelling apparatus according to claim 6,
wherein the engaging portion and the engaged portion are hooks that are disengageable from each other.

9. The tissue fastening tool indwelling apparatus according to claim 6,
wherein the engaging portion is a projection that projects at an angle with respect to the axis of the tissue fastening tool or the stylet, and the engaged portion has a shape for engagement with the projection.

10. The tissue fastening apparatus according to claim 1,
wherein one of an end of the tissue fastening tool and a distal end of the stylet is formed in a tubular shape having an inner cavity and forming a through hole at an outer peripheral surface thereof, and the other is advanced into the inner cavity and engaged with the through hole, whereby the tissue fastening tool and the stylet are connected together.

11. The tissue fastening apparatus according to claim 10, wherein the end face of the tubular part is formed so that the longitudinal dimension of the outer peripheral surface where the through hole is provided becomes the longest.

12. The tissue fastening apparatus according to claim 1, wherein one of the end of the tissue fastening tool and a distal end of the stylet has a through hole having a larger diameter than the other, and the other is advanced into the through hole, whereby the tissue fastening tool and the stylet are connected together.

13. The tissue fastening tool indwelling apparatus according to claim 1, wherein, if the rotation mechanism rotates the stylet one rotation around an axis, the stylet advances and retreat inside the needle tube so that the tissue fastening tool is inserted and pushed the needle tube by a length equivalent to one coil turn.

14. The tissue fastening tool indwelling apparatus according to claim 1, wherein the connecting section is connected with the tissue fastening tool in the lumen, and the connecting section includes a movement member that moves in a direction which a connection mode between the connecting section and the tissue fastening tool being released at the level of the lumen protruding from the opening with which the lumen being communicated.

* * * * *